United States Patent
Burgess et al.

(10) Patent No.: US 9,556,157 B2
(45) Date of Patent: Jan. 31, 2017

(54) ENHANCER OF ZESTE HOMOLOG 2 INHIBITORS

(71) Applicant: GlaxoSmithKline Intellectual Property (No.2) Limited, Brentford, Middlesex (GB)

(72) Inventors: Joelle Lorraine Burgess, Collegeville, PA (US); Steven David Knight, Collegeville, PA (US)

(73) Assignee: GlaxoSmithKline Intellectual Property (No.2) Limited, Brentford, Middlesex (GB)

( * ) Notice: Subject to any disclaimer, the term of this patent is extended or adjusted under 35 U.S.C. 154(b) by 0 days.

(21) Appl. No.: 14/898,178

(22) PCT Filed: Jul. 9, 2014

(86) PCT No.: PCT/IB2014/062983
§ 371 (c)(1),
(2) Date: Dec. 14, 2015

(87) PCT Pub. No.: WO2015/004618
PCT Pub. Date: Jan. 15, 2015

(65) Prior Publication Data
US 2016/0130261 A1 May 12, 2016

Related U.S. Application Data

(60) Provisional application No. 61/844,540, filed on Jul. 10, 2013.

(51) Int. Cl.
*C07D 409/12* (2006.01)
*C07D 409/14* (2006.01)
*A61K 31/4436* (2006.01)

(52) U.S. Cl.
CPC ........... *C07D 409/14* (2013.01); *C07D 409/12* (2013.01)

(58) Field of Classification Search
None
See application file for complete search history.

(56) References Cited

U.S. PATENT DOCUMENTS

| 8,410,088 | B2 | 4/2013 | Kuntz et al. |
|---|---|---|---|
| 8,536,179 | B2 | 9/2013 | Miller et al. |
| 8,598,167 | B1 | 12/2013 | Kuntz et al. |
| 8,637,509 | B2 | 1/2014 | Burgess et al. |
| 8,765,732 | B2 | 7/2014 | Kuntz et al. |
| 8,765,792 | B2 | 7/2014 | Knight et al. |
| 8,846,935 | B2 | 9/2014 | Duquenne et al. |
| 9,006,242 | B2 | 4/2015 | Kuntz et al. |
| 2002/0025960 | A1 | 2/2002 | Bundy et al. |
| 2006/0094708 | A1 | 5/2006 | Qian et al. |
| 2009/0181983 | A1 | 7/2009 | Corte, Jr. |
| 2012/0209012 | A1 | 8/2012 | McDonald et al. |
| 2012/0264734 | A1 | 10/2012 | Kuntz et al. |
| 2013/0053383 | A1 | 2/2013 | Duquenne et al. |
| 2013/0245016 | A1 | 9/2013 | Knight et al. |
| 2013/0345200 | A1 | 12/2013 | Brackley et al. |
| 2014/0107122 | A1 | 4/2014 | Kuntz et al. |
| 2014/0142083 | A1 | 5/2014 | Kuntz et al. |
| 2015/0051163 | A1 | 2/2015 | Keilhack et al. |
| 2015/0126522 | A1 | 5/2015 | Burgess et al. |
| 2015/0307480 | A1 | 10/2015 | Knight et al. |

FOREIGN PATENT DOCUMENTS

| WO | WO 2011/140324 A1 | 11/2011 |
|---|---|---|
| WO | WO 2012/005805 A1 | 1/2012 |
| WO | WO 2012/118812 A2 | 9/2012 |
| WO | WO 2012/142504 A1 | 10/2012 |
| WO | WO 2013/049770 A2 | 4/2013 |
| WO | WO 2013/120104 A2 | 8/2013 |
| WO | WO 2013/155317 A1 | 10/2013 |
| WO | WO 2014/177982 A1 | 11/2014 |
| WO | WO 2015/010049 A1 | 1/2015 |

OTHER PUBLICATIONS

Konze, et al. ACS Chemical Biology, 8(6): 1324-1334, Jun. 21, 2013.

*Primary Examiner* — Zinna Northington Davis
(74) *Attorney, Agent, or Firm* — Duke M. Fitch; Kathryn A. Lutomski; Edward R. Gimmi

(57) ABSTRACT

This invention relates to novel compounds according to Formula (I) which are inhibitors of Enhancer of Zeste Homolog 2 (EZH2), to pharmaceutical compositions containing them, to processes for their preparation, and to their use in therapy for the treatment of cancers.

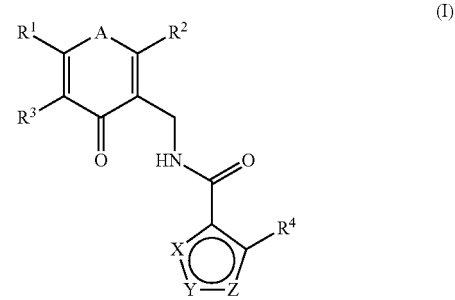

20 Claims, No Drawings

ENHANCER OF ZESTE HOMOLOG 2 INHIBITORS

This application is a §371 of International Application No. PCT/IB2014/062983, filed 9 Jul. 2014, which claims the priority of U.S. Provisional Application No. 61/844,540, filed 10 Jul. 2013.

FIELD OF THE INVENTION

This invention relates to compounds which inhibit Enhancer of Zeste Homolog 2 (EZH2) and thus are useful for inhibiting the proliferation of and/or inducing apoptosis in cancer cells.

BACKGROUND OF THE INVENTION

Epigenetic modifications play an important role in the regulation of many cellular processes including cell proliferation, differentiation, and cell survival. Global epigenetic modifications are common in cancer, and include global changes in DNA and/or histone methylation, dysregulation of non-coding RNAs and nucleosome remodeling leading to aberrant activation or inactivation of oncogenes, tumor suppressors and signaling pathways. However, unlike genetic mutations which arise in cancer, these epigenetic changes can be reversed through selective inhibition of the enzymes involved. Several methylases involved in histone or DNA methylation are known to be dysregulated in cancer. Thus, selective inhibitors of particular methylases will be useful in the treatment of proliferative diseases such as cancer.

EZH2 (human EZH2 gene: Cardoso, C, et al; *European J of Human Genetics*, Vol. 8, No. 3 Pages 174-180, 2000) is the catalytic subunit of the Polycomb Repressor Complex 2 (PRC2) which functions to silence target genes by trimethylating lysine 27 of histone H3 (H3K27me3). Histone H3 is one of the five main histone proteins involved in the structure of chromatin in eukaryotic cells. Featuring a main globular domain and a long N-terminal tail, Histones are involved with the structure of the nucleosomes, a 'beads on a string' structure. Histone proteins are highly post-translationally modified however Histone H3 is the most extensively modified of the five histones. The term "Histone H3" alone is purposely ambiguous in that it does not distinguish between sequence variants or modification state. Histone H3 is an important protein in the emerging field of epigenetics, where its sequence variants and variable modification states are thought to play a role in the dynamic and long term regulation of genes.

Increased EZH2 expression has been observed in numerous solid tumors including those of the prostate, breast, skin, bladder, liver, pancreas, head and neck and correlates with cancer aggressiveness, metastasis and poor outcome (Varambally et al., 2002; Kleer et al., 2003; Breuer et al., 2004; Bachmann et al., 2005; Weikert et al., 2005; Sudo et al., 2005; Bachmann et al., 2006). For instance, there is a greater risk of recurrence after prostatectomy in tumors expressing high levels of EZH2, increased metastasis, shorter disease-free survival and increased death in breast cancer patients with high EZH2 levels (Varambally et al., 2002; Kleer et al., 2003). More recently, inactivating mutations in UTX (ubiquitously transcribed tetratricopeptide repeats X), a H3K27 demethylase which functions in opposition to EZH2, have been identified in multiple solid and hematological tumor types (including renal, glioblastoma, esophageal, breast, colon, non-small cell lung, small cell lung, bladder, multiple myeloma, and chronic myeloid leukemia tumors), and low UTX levels correlate with poor survival in breast cancer suggesting that loss of UTX function leads to increased H3K27me3 and repression of target genes (Wang et al., 2010). Together, these data suggest that increased H3K27me3 levels contribute to cancer aggressiveness in many tumor types and that inhibition of EZH2 activity may provide therapeutic benefit.

Numerous studies have reported that direct knockdown of EZH2 via siRNA or shRNA or indirect loss of EZH2 via treatment with the SAH hydrolase inhibitor 3-deazaneplanocin A (DZNep) decreases cancer cell line proliferation and invasion in vitro and tumor growth in vivo (Gonzalez et al., 2008, GBM 2009). While the precise mechanism by which aberrant EZH2 activity leads to cancer progression is not known, many EZH2 target genes are tumor suppressors suggesting that loss of tumor suppressor function is a key mechanism. In addition, EZH2 overexpression in immortalized or primary epithelial cells promotes anchorage independent growth and invasion and requires EZH2 catalytic activity (Kleer et al., 2003; Cao et al., 2008).

Thus, there is strong evidence to suggest that inhibition of EZH2 activity decreases cellular proliferation and invasion. Accordingly, compounds that inhibit EZH2 activity would be useful for the treatment of cancer.

SUMMARY OF THE INVENTION

The present invention relates to compounds according to Formula (I):

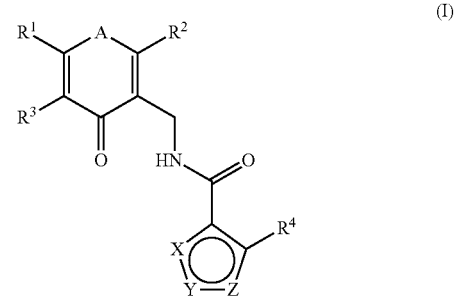

wherein:

A is O or NH;

X is O, N, S, $CR^6$, or $NR^7$;

Y is O, N, S, $CR^6$, or $NR^7$;

Z is $CR^5$ or $NR^8$; wherein when X is O, S, or $NR^7$, Y is N or $CR^6$ and Z is $CR^5$; when Y is O, S, or $NR^7$, X is N or $CR^6$ and Z is $CR^5$; and when Z is $NR^8$, Y is N or $CR^6$ and X is N or $CR^6$;

$R^1$, $R^2$, and $R^3$ are each independently selected from the group consisting of hydrogen, $(C_1-C_4)$alkoxy, $(C_1-C_8)$alkyl, $(C_1-C_4)$alkoxy$(C_1-C_4)$alkyl-, halo$(C_1-C_4)$alkyl, $(C_3-C_8)$cycloalkyl, hydroxy$(C_1-C_4)$alkyl, $(C_3-C_8)$cycloalkyl$(C_1-C_4)$alkyl-, $R^aO(O)CNH(C_1-C_4)$alkyl-, $(C_6-C_{10})$bicycloalkyl, heterocycloalkyl, heterocycloalkyl$(C_1-C_4)$alkyl-, aryl, aryl$(C_1-C_4)$alkyl, heteroaryl, heteroaryl$(C_1-C_4)$alkyl, halogen, cyano, —C(O)$R^a$, —CO$_2R^a$, —C(O)NR$^a$R$^b$, —C(O)NR$^a$NR$^b$, —S(O)$R^a$, —SO$_2R^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2R^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —NR$^a$NR$^a$C(O)OR$^a$, —OR$^a$, —OC(O)R$^a$, and —OC(O)NR$^a$R$^b$, wherein each $(C_3-C_8)$cycloalkyl, $(C_6-C_{10})$bicycloalkyl, heterocycloalkyl, aryl, or heteroaryl is optionally substituted 1, 2, or 3 times, independently, by hydroxyl, halogen, nitro, $(C_1-C_4)$alkyl, cyano, $(C_1-C_4)$alkoxy, —$NR^aR^b$ or —$CO_2R^a$;

$R^4$ is selected from the group consisting of hydrogen, $(C_1-C_3)$alkoxy, $(C_1-C_3)$alkyl, hydroxyl, halogen, cyano, $(C_3-C_6)$cycloalkyl, heterocycloalkyl, —$NR^aR^b$, halo$(C_1-C_3)$alkyl, and hydroxy$(C_1-C_3)$alkyl;

$R^5$ is selected from the group consisting of $(C_4-C_8)$alkyl, $(C_2-C_8)$alkenyl, $(C_3-C_8)$alkoxy, $(C_4-C_8)$cycloalkyl, $(C_3-C_8)$cycloalkyl$(C_1-C_2)$alkyl-, $(C_3-C_8)$cycloalkyloxy-, heterocycloalkyl, heterocycloalkyl$(C_1-C_2)$alkyl-, heterocycloalkyloxy-, aryl, heteroaryl, and —$NR^aR^b$, wherein said $(C_4-C_8)$alkyl, $(C_2-C_8)$alkenyl, $(C_3-C_8)$alkoxy, $(C_4-C_8)$cycloalkyl, $(C_3-C_8)$cycloalkyl$(C_1-C_2)$alkyl-, $(C_3-C_8)$cycloalkyloxy-, heterocycloalkyl, heterocycloalkyl$(C_1-C_2)$alkyl-, heterocycloalkyloxy-, aryl, or heteroaryl is optionally substituted 1, 2, or 3 times, independently, by halogen, —$OR^a$, —$NR^aR^b$, —$NHCO_2R^a$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —$CO_2R^a$, —$C(O)NR^aR^b$, —$SO_2NR^aR^b$, heterocycloalkyl, aryl, or heteroaryl, wherein said $(C_3-C_8)$cycloalkyl, heterocycloalkyl, aryl, or heteroaryl is optionally substituted 1 or 2 times, independently, by halogen, $(C_1-C_4)$alkyl, halo$(C_1-C_4)$alkyl, —$CO(C_1-C_4)$alkyl, —$CO_2(C_1-C_4)$alkyl, —$NR^aR^b$, —$NHCO_2R^a$, hydroxyl, oxo, $(C_1-C_4)$alkoxy, or $(C_1-C_4)$alkoxy$(C_1-C_4)$alkyl-; or any 2 optional substituents on said $(C_2-C_8)$alkenyl taken together with the carbon atom(s) to which they are attached represent a 5-8 membered ring, optionally containing a heteroatom selected from oxygen, nitrogen, and sulfur, wherein said ring is optionally substituted 1 or 2 times, independently, by $(C_1-C_4)$alkyl, halo$(C_1-C_4)$alkyl, —$CO(C_1-C_4)$alkyl, —$CO_2(C_1-C_4)$alkyl, —$NR^aR^b$, —$NHCO_2R^a$, hydroxyl, oxo, $(C_1-C_4)$alkoxy, or $(C_1-C_4)$alkoxy$(C_1-C_4)$alkyl-;

$R^6$ is selected from the group consisting of hydrogen, halogen, $(C_1-C_8)$alkyl, $(C_1-C_4)$alkoxy, —$B(OH)_2$, $(C_3-C_8)$cycloalkyl, $(C_3-C_8)$cycloalkyl$(C_1-C_4)$alkyl-, $(C_6-C_{10})$bicycloalkyl, heterocycloalkyl, heterocycloalkyl$(C_1-C_4)$alkyl-, aryl, aryl$(C_1-C_4)$alkyl, heteroaryl, heteroaryl$(C_1-C_4)$alkyl, cyano, —$C(O)R^a$, —$CO_2R^a$, —$C(O)NR^aR^b$, —$C(O)NR^aN$-$R^aR^b$, —$SR^a$, —$S(O)R^a$, —$SO_2R^a$, —$SO_2NR^aR^b$, nitro, —$NR^aR^b$, $R^aR^bN(C_1-C_4)$alkyl-, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$, wherein each cycloalkyl, bicycloalkyl, heterocycloalkyl, aryl, or heteroaryl group is optionally substituted 1, 2, or 3 times, independently, by $R^c$—$(C_1-C_6)$alkyl-$O$—, $(C_1-C_4)$alkyl-heterocycloalkyl-, halogen, $(C_1-C_6)$alkyl, $(C_3-C_8)$cycloalkyl, halo$(C_1-C_6)$alkyl, cyano, —$C(O)R^a$, —$CO_2R^a$, —$C(O)NR^aR^b$, —$SR^a$, —$S(O)R^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, or heteroaryl$(C_1-C_4)$alkyl;

$R^7$ is selected from the group consisting of hydrogen, $(C_1-C_8)$alkyl, $(C_3-C_8)$cycloalkyl, $(C_3-C_8)$cycloalkyl$(C_1-C_4)$alkyl-, $(C_6-C_{10})$bicycloalkyl, heterocycloalkyl, heterocycloalkyl$(C_1-C_4)$alkyl-, aryl, aryl$(C_1-C_4)$alkyl, heteroaryl, heteroaryl$(C_1-C_4)$alkyl, —$C(O)R^a$, —$CO_2R^a$, —$C(O)NR^aR^b$, —$C(O)NR^aNR^aR^b$, —$SO_2R^a$, —$SO_2NR^aR^b$, and $R^aR^bN(C_1-C_4)$alkyl-, wherein each cycloalkyl, bicycloalkyl, heterocycloalkyl, aryl, or heteroaryl group is optionally substituted 1, 2, or 3 times, independently, by $R^c$—$(C_1-C_6)$alkyl-$O$—, $R^c$—$(C_1-C_6)$alkyl-$S$—, $R^c$—$(C_1-C_6)$alkyl-, $(C_1-C_4)$alkyl-heterocycloalkyl-, halogen, $(C_1-C_6)$alkyl, $(C_3-C_8)$cycloalkyl, halo$(C_1-C_6)$alkyl, cyano, —$C(O)R^a$, —$CO_2R^a$, —$C(O)NR^aR^b$, —$SR^a$, —$S(O)R^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, or heteroaryl$(C_1-C_4)$alkyl;

$R^8$ is selected from the group consisting of $(C_4-C_8)$alkyl, $(C_4-C_8)$cycloalkyl, heterocycloalkyl, heterocycloalkyl$(C_1-C_2)$alkyl-, aryl, and heteroaryl, wherein said $(C_4-C_8)$alkyl, $(C_4-C_8)$cycloalkyl, heterocycloalkyl, heterocycloalkyl$(C_1-C_2)$alkyl-, aryl, or heteroaryl is optionally substituted 1, 2, or 3 times, independently, by halogen, —$OR^a$, —$NR^aR^b$, —$NHCO_2R^a$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —$CO_2R^a$, —$C(O)NR^aR^b$, —$SO_2NR^aR^b$, aryl, or heteroaryl;

each $R^c$ is independently —$S(O)R^a$, —$SO_2R^a$, —$NR^aR^b$, —$NR^aC(O)OR^a$, —$NR^aSO_2R^b$, or —$CO_2R^a$; and $R^a$ and $R^b$ are each independently hydrogen, $(C_1-C_4)$alkyl, $(C_1-C_4)$alkoxy$(C_1-C_4)$alkyl-, $(C_3-C_{10})$cycloalkyl, heterocycloalkyl, aryl, aryl$(C_1-C_4)$alkyl-, heteroaryl$(C_1-C_4)$alkyl-, or heteroaryl, wherein any said cycloalkyl, heterocycloalkyl, aryl, or heteroaryl group is optionally substituted 1, 2, or 3 times, independently, by halogen, hydroxyl, $(C_1-C_4)$alkoxy, amino, —$NH(C_1-C_4)$alkyl, —$N((C_1-C_4)$alkyl$)_2$, $(C_1-C_4)$alkyl, halo$(C_1-C_4)$alkyl, —$CO_2H$, —$CO_2(C_1-C_4)$alkyl, —$CONH_2$, —$CONH(C_1-C_4)$alkyl, —$CON((C_1-C_4)$alkyl$)_2$, —$SO_2(C_1-C_4)$alkyl, —$SO_2NH_2$, —$SO_2NH(C_1-C_4)$alkyl, or —$SO_2N((C_1-C_4)$alkyl$)_2$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted 1, 2, or 3 times, independently, by $(C_1-C_4)$alkyl, halo$(C_1-C_4)$alkyl, amino, —$NH(C_1-C_4)$alkyl, —$N((C_1-C_4)$alkyl$)_2$, hydroxyl, oxo, $(C_1-C_4)$alkoxy, or $(C_1-C_4)$alkoxy$(C_1-C_4)$alkyl-, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

or pharmaceutically acceptable salts thereof.

Another aspect of this invention relates to a method of inducing apoptosis in cancer cells of solid tumors; treating solid tumor cancers.

Another aspect of the invention relates to pharmaceutical preparations comprising compounds of Formula (I) and pharmaceutically acceptable excipients.

In another aspect, there is provided the use of a compound of Formula (I) and/or a pharmaceutically acceptable salt or solvate thereof, in the preparation of a medicament for use in the treatment of a disorder mediated by EZH2, such as by inducing apoptosis in cancer cells.

In another aspect, this invention provides for the use of a compound of Formula (I) or a pharmaceutically acceptable salt thereof for the treatment of diseases mediated by EZH2. The invention further provides for the use of a compound of Formula (I) or a pharmaceutically acceptable salt thereof as an active therapeutic substance in the treatment of a disease mediated by EZH2.

In another aspect, the invention provides a compound of Formula (I) or a pharmaceutically acceptable salt thereof for use in therapy.

In another aspect there is provided methods of co-administering the presently invented compounds of Formula (I) with other active ingredients.

DETAILED DESCRIPTION OF THE INVENTION

This invention relates to compounds of the Formula (I) as defined above.

In one embodiment, this invention relates to compounds of Formula (I), wherein:

A is O or NH;

X is O, N, S, $CR^6$, or $NR^7$;

Y is O, N, S, $CR^6$, or $NR^7$;

Z is $CR^5$ or $NR^8$; wherein when X is O, S, or $NR^7$, Y is N or $CR^6$ and Z is $CR^5$; when Y is O, S, or $NR^7$, X is N or $CR^6$ and Z is $CR^5$; and when Z is $NR^8$, Y is N or $CR^6$ and X is N or $CR^6$;

$R^1$, $R^2$, and $R^3$ are each independently selected from the group consisting of hydrogen, $(C_1-C_4)$alkoxy, $(C_1-C_8)$alkyl, $(C_1-C_4)$alkoxy$(C_1-C_4)$alkyl-, halo$(C_1-C_4)$alkyl, $(C_3-C_8)$cycloalkyl, hydroxy$(C_1-C_4)$alkyl, $(C_3-C_8)$cycloalkyl$(C_1-C_4)$alkyl-, $R^aO(O)CNH(C_1-C_4)$alkyl-, $(C_6-C_{10})$bicycloalkyl, heterocycloalkyl, heterocycloalkyl$(C_1-C_4)$alkyl-, aryl, aryl$(C_1-C_4)$alkyl, heteroaryl, heteroaryl$(C_1-C_4)$alkyl, halogen, cyano, —C(O)$R^a$, —CO$_2R^a$, —C(O)$NR^aR^b$, —C(O)$NR^aNR^aR^b$, —S(O)$R^a$, —SO$_2R^a$, —SO$_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aN$-$R^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$, wherein each $(C_3-C_8)$cycloalkyl, $(C_6-C_{10})$bicycloalkyl, heterocycloalkyl, aryl, or heteroaryl is optionally substituted 1, 2, or 3 times, independently, by hydroxyl, halogen, nitro, $(C_1-C_4)$alkyl, cyano, $(C_1-C_4)$alkoxy, —$NR^aR^b$ or —$CO_2R^a$;

$R^4$ is selected from the group consisting of hydrogen, $(C_1-C_3)$alkoxy, $(C_1-C_3)$alkyl, hydroxyl, halogen, cyano, $(C_3-C_6)$cycloalkyl, heterocycloalkyl, —$NR^aR^b$, halo$(C_1-C_3)$alkyl, and hydroxy$(C_1-C_3)$alkyl;

$R^5$ is selected from the group consisting of $(C_4-C_8)$alkyl, $(C_3-C_8)$alkoxy, $(C_4-C_8)$cycloalkyl, $(C_3-C_8)$cycloalkyloxy-, heterocycloalkyl, heterocycloalkyloxy-, aryl, heteroaryl, and —$NR^aR^b$, wherein said $(C_4-C_8)$alkyl, $(C_3-C_8)$alkoxy, $(C_4-C_8)$cycloalkyl, $(C_3-C_8)$cycloalkyloxy-, heterocycloalkyl, heterocycloalkyloxy-, aryl, or heteroaryl is optionally substituted 1, 2, or 3 times, independently, by halogen, —$OR^a$, —$NR^aR^b$, —$NHCO_2R^a$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —$CO_2R^a$, —$C(O)NR^aR^b$, —$SO_2NR^aR^b$, aryl, or heteroaryl;

$R^6$ is selected from the group consisting of hydrogen, halogen, $(C_1-C_8)$alkyl, $(C_1-C_4)$alkoxy, —$B(OH)_2$, $(C_3-C_8)$cycloalkyl, $(C_3-C_8)$cycloalkyl$(C_1-C_4)$alkyl-, $(C_6-C_{10})$bicycloalkyl, heterocycloalkyl, heterocycloalkyl$(C_1-C_4)$alkyl-, aryl, aryl$(C_1-C_4)$alkyl, heteroaryl, heteroaryl$(C_1-C_4)$alkyl, cyano, —$C(O)R^a$, —$CO_2R^a$, —$C(O)NR^aR^b$, —$C(O)NR^aN$-$R^aR^b$, —$SR^a$, —$S(O)R^a$, —$SO_2R^a$, —$SO_2NR^aR^b$, nitro, —$NR^aR^b$, $R^aR^bN(C_1-C_4)$alkyl-, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$, wherein each cycloalkyl, bicycloalkyl, heterocycloalkyl, aryl, or heteroaryl group is optionally substituted 1, 2, or 3 times, independently, by $R^c$—$(C_1-C_6)$alkyl-O—, $(C_1-C_4)$alkyl-heterocycloalkyl-, halogen, $(C_1-C_6)$alkyl, $(C_3-C_8)$cycloalkyl, halo$(C_1-C_6)$alkyl, cyano, —$C(O)R^a$, —$CO_2R^a$, —$C(O)NR^aR^b$, —$S(O)R^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, or heteroaryl$(C_1-C_4)$alkyl;

$R^7$ is selected from the group consisting of hydrogen, $(C_1-C_8)$alkyl, $(C_3-C_8)$cycloalkyl, $(C_3-C_8)$cycloalkyl$(C_1-C_4)$alkyl-, $(C_6-C_{10})$bicycloalkyl, heterocycloalkyl, heterocycloalkyl$(C_1-C_4)$alkyl-, aryl, aryl$(C_1-C_4)$alkyl, heteroaryl, heteroaryl$(C_1-C_4)$alkyl, —$C(O)R^a$, —$CO_2R^a$, —$C(O)NR^aR^b$, —$C(O)NR^aNR^aR^b$, —$SO_2R^a$, —$SO_2NR^aR^b$, and $R^aR^bN(C_1-C_4)$alkyl-, wherein each cycloalkyl, bicycloalkyl, heterocycloalkyl, aryl, or heteroaryl group is optionally substituted 1, 2, or 3 times, independently, by $R^c$—$(C_1-C_6)$alkyl-O—, $(C_1-C_4)$alkyl-heterocycloalkyl-, halogen, $(C_1-C_6)$alkyl, $(C_3-C_8)$cycloalkyl, halo$(C_1-C_6)$alkyl, cyano, —$C(O)R^a$, —$CO_2R^a$, —$C(O)NR^aR^b$, —$S(O)R^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, or heteroaryl$(C_1-C_4)$alkyl;

$R^8$ is selected from the group consisting of $(C_4-C_8)$alkyl, $(C_4-C_8)$cycloalkyl, heterocycloalkyl, aryl, and heteroaryl, wherein said $(C_4-C_8)$alkyl, $(C_4-C_8)$cycloalkyl, heterocycloalkyl, aryl, or heteroaryl is optionally substituted 1, 2, or 3 times, independently, by halogen, —$OR^a$, —$NR^aR^b$, —$NHCO_2R^a$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —$CO_2R^a$, —$C(O)NR^aR^b$, —$SO_2NR^aR^b$, aryl, or heteroaryl;

each $R^c$ is independently —$S(O)R^a$, —$SO_2R^a$, —$NR^aR^b$, —$NR^aC(O)OR^a$, —$NR^aSO_2R^b$, or —$CO_2R^a$; and $R^a$ and $R^b$ are each independently hydrogen, $(C_1-C_4)$alkyl, $(C_1-C_4)$alkoxy$(C_1-C_4)$alkyl-, $(C_3-C_{10})$cycloalkyl, heterocycloalkyl, aryl, aryl$(C_1-C_4)$alkyl-, heteroaryl$(C_1-C_4)$alkyl-, or heteroaryl, wherein any said cycloalkyl, heterocycloalkyl, aryl, or heteroaryl group is optionally substituted 1, 2, or 3 times, independently, by halogen, hydroxyl, $(C_1-C_4)$alkoxy, amino, —$NH(C_1-C_4)$alkyl, —$N((C_1-C_4)$alkyl$)_2$, $(C_1-C_4)$alkyl, halo$(C_1-C_4)$alkyl, —$CO_2H$, —$CO_2(C_1-C_4)$alkyl, —$CONH_2$, —$CONH(C_1-C_4)$alkyl, —$CON((C_1-C_4)$alkyl$)_2$, —$SO_2(C_1-C_4)$alkyl, —$SO_2NH_2$, —$SO_2NH(C_1-C_4)$alkyl, or —$SO_2N((C_1-C_4)$alkyl$)_2$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted 1, 2, or 3 times, independently, by $(C_1-C_4)$alkyl, halo$(C_1-C_4)$alkyl, amino, —NH$(C_1-C_4)$alkyl, —$N((C_1-C_4)$alkyl$)_2$, hydroxyl, oxo, $(C_1-C_4)$alkoxy, or $(C_1-C_4)$alkoxy$(C_1-C_4)$alkyl-, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring; or pharmaceutically acceptable salts thereof.

In one embodiment, this invention relates to compounds of Formula (I), wherein A is NH. In another embodiment, this invention relates to compounds of Formula (I), wherein A is O.

In one embodiment, this invention relates to compounds of Formula (I), wherein X is O, S, or $NR^7$; Y is N or $CR^6$; and Z is $CR^5$. In another embodiment, this invention relates to compounds of Formula (I), wherein X is O or S; Y is N or $CR^6$; and Z is $CR^5$. In another embodiment, this invention relates to compounds of Formula (I), wherein X is O or S; Y is $CR^6$; and Z is $CR^5$. In another embodiment, this invention relates to compounds of Formula (I), wherein X is O or S; Y is N; and Z is $CR^5$. In another embodiment, this invention relates to compounds of Formula (I), wherein X is S; Y is $CR^6$; and Z is $CR^5$. In another embodiment, this invention relates to compounds of Formula (I), wherein Y is O, S, or $NR^7$; X is N or $CR^6$; and Z is $CR^5$. In another embodiment, this invention relates to compounds of Formula (I), wherein Y is O or S; X is N or $CR^6$; and Z is $CR^5$. In another embodiment, this invention relates to compounds of Formula (I), wherein Y is O or S; X is $CR^6$; and Z is $CR^5$. In another embodiment, this invention relates to compounds of Formula (I), wherein Y is O or S; X is N; and Z is $CR^5$. In another embodiment, this invention relates to compounds of Formula (I), wherein Y is S; X is $CR^6$; and Z is $CR^5$. In another embodiment, this invention relates to compounds of Formula (I), wherein Z is $NR^8$; Y is N or $CR^6$; and X is N or $CR^6$.

In another embodiment, this invention relates to compounds of Formula (I), wherein $R^1$, $R^2$, and $R^3$ are each independently selected from the group consisting of hydrogen, $(C_1-C_4)$alkoxy, $(C_1-C_4)$alkyl, $(C_1-C_4)$alkoxy$(C_1-C_4)$alkyl-, halo$(C_1-C_4)$alkyl, $(C_3-C_8)$cycloalkyl, hydroxy$(C_1-C_4)$alkyl, $(C_3-C_8)$cycloalkyl$(C_1-C_4)$alkyl-, $(C_1-C_4)$alkylO(O)CNH$(C_1-C_4)$alkyl-, amino, —NH$(C_1-C_4)$alkyl, —N$((C_1-C_4)$alkyl$)_2$, heterocycloalkyl, heterocycloalkyl$(C_1-C_4)$alkyl-, aryl, aryl$(C_1-C_4)$alkyl-, heteroaryl, and heteroaryl$(C_1-C_4)$alkyl-, wherein each $(C_3-C_8)$cycloalkyl, heterocycloalkyl, aryl, or heteroaryl is optionally substituted 1 or 2 times, independently, by hydroxyl, halogen, nitro, $(C_1-C_4)$alkyl, cyano, $(C_1-C_4)$alkoxy, —NH$(C_1-C_4)$alkyl, —N$((C_1-C_4)$alkyl$)_2$, or —CO$_2(C_1-C_4)$alkyl. In another embodiment, this invention relates to compounds of Formula (I), wherein $R^1$, $R^2$, and $R^3$ are each independently selected from the group consisting of hydrogen, $(C_1-C_4)$alkoxy, $(C_1-C_4)$alkyl, $(C_1-C_4)$alkoxy$(C_1-C_4)$alkyl-, halo$(C_1-C_4)$alkyl, hydroxy$(C_1-C_4)$alkyl, amino, —NH$(C_1-C_4)$alkyl, and —N$((C_1-C_4)$alkyl$)_2$.

In another embodiment, this invention relates to compounds of Formula (I), wherein $R^1$ and $R^2$ are each independently $(C_1-C_4)$alkyl.

In a specific embodiment, this invention relates to compounds of Formula (I), wherein $R^1$ is methyl.

In another specific embodiment, this invention relates to compounds of Formula (I), wherein $R^2$ is methyl.

In another specific embodiment, this invention relates to compounds of Formula (I), wherein $R^1$ and $R^2$ are each methyl.

In another embodiment, this invention relates to compounds of Formula (I), wherein $R^3$ is hydrogen, amino, —NH$(C_1-C_4)$alkyl, or —N$((C_1-C_4)$alkyl$)_2$. In a specific embodiment, this invention relates to compounds of Formula (I), wherein $R^3$ is amino. In another specific embodiment, this invention relates to compounds of Formula (I), wherein $R^3$ is hydrogen.

In another embodiment, this invention relates to compounds of Formula (I), wherein $R^4$ is selected from the group consisting of hydrogen, $(C_1-C_3)$alkyl, hydroxyl, halogen, halo$(C_1-C_3)$alkyl, and hydroxy$(C_1-C_3)$alkyl. In another embodiment, this invention relates to compounds of Formula (I), wherein $R^4$ is $(C_1-C_3)$alkyl or halogen. In a specific embodiment, this invention relates to compounds of Formula (I), wherein $R^4$ is methyl or chlorine. In another specific embodiment, this invention relates to compounds of Formula (I), wherein $R^4$ is methyl.

In another embodiment, this invention relates to compounds of Formula (I), wherein $R^5$ is selected from the group consisting of $(C_3-C_6)$alkoxy, $(C_3-C_6)$cycloalkyloxy-, heterocycloalkyloxy-, heterocycloalkyl, —NH$((C_3-C_6)$cycloalkyl), —N$((C_1-C_3)$alkyl)$((C_3-C_6)$cycloalkyl), —NH(heterocycloalkyl), and —N$((C_1-C_3)$alkyl)(heterocycloalkyl), wherein any said $(C_3-C_6)$alkoxy, $(C_3-C_6)$cycloalkyloxy-, heterocycloalkyloxy-, heterocycloalkyl, or $(C_3-C_6)$cycloalkyl is optionally substituted 1 or 2 times, independently, by halogen, hydroxyl, $(C_1-C_3)$alkoxy, amino, —NH$(C_1-C_3)$alkyl, —N$((C_1-C_3)$alkyl$)_2$, $(C_1-C_3)$alkyl, $(C_1-C_3)$alkoxy$(C_1-C_3)$alkyl-, amino$(C_1-C_3)$alkyl-, $((C_1-C_3)$alkyl)NH$(C_1-C_3)$alkyl-, $((C_1-C_3)$alkyl$)_2$N$(C_1-C_3)$alkyl-, $(C_3-C_8)$cycloalkyl, cyano, —CO$_2R^a$, —C(O)NR$^a$R$^b$, —SO$_2$NR$^a$R$^b$, phenyl, or heteroaryl.

In another embodiment, this invention relates to compounds of Formula (I), wherein $R^5$ is selected from the group consisting of $(C_3-C_6)$alkoxy, $(C_3-C_8)$cycloalkyloxy-, and heterocycloalkyloxy-, each of which is optionally substituted by hydroxyl, $(C_1-C_3)$alkoxy, amino, —NH$(C_1-C_3)$alkyl, —N$((C_1-C_3)$alkyl$)_2$, $(C_1-C_3)$alkyl, —CO$_2R^a$, —C(O)NR$^a$R$^b$, —SO$_2$NR$^a$R$^b$, phenyl, or heteroaryl.

In another embodiment, this invention relates to compounds of Formula (I), wherein $R^5$ is $(C_3-C_6)$cycloalkyloxy- which is optionally substituted 1, 2, or 3 times, independently, by halogen, —OR$^7$, —NR$^a$R$^b$, nitro, $(C_1-C_3)$alkyl, R$^a$R$^b$N$(C_1-C_3)$alkyl-, R$^a$O$(C_1-C_3)$alkyl-, $(C_3-C_8)$cycloalkyl, cyano, —CO$_2R^a$, —C(O)NR$^a$R$^b$, —SO$_2$NR$^a$R$^b$, aryl, or heteroaryl. In another embodiment, this invention relates to compounds of Formula (I), wherein $R^5$ is $(C_3-C_6)$cycloalkyloxy- which is optionally substituted 1 or 2 times, independently, by halogen, hydroxyl, $(C_1-C_3)$alkoxy, amino, —NH$(C_1-C_3)$alkyl, —N$((C_1-C_3)$alkyl$)_2$, $(C_1-C_3)$alkyl, $(C_1-C_3)$alkoxy$(C_1-C_3)$alkyl-, amino$(C_1-C_3)$alkyl-, $((C_1-C_3)$alkyl)NH$(C_1-C_3)$alkyl-, $((C_1-C_3)$alkyl$)_2$N$(C_1-C_3)$alkyl-, $(C_3-C_8)$cycloalkyl, cyano, —CO$_2R^a$, —C(O)NR$^a$R$^b$, —SO$_2$NR$^a$R$^b$, phenyl, or heteroaryl.

In another embodiment, this invention relates to compounds of Formula (I), wherein $R^5$ is heterocycloalkyloxy- which is optionally substituted 1, 2, or 3 times, independently, by halogen, —OR$^a$, —NR$^a$R$^b$, nitro, $(C_1-C_3)$alkyl, R$^a$R$^b$N$(C_1-C_3)$alkyl-, R$^a$O$(C_1-C_3)$alkyl-, $(C_3-C_8)$cycloalkyl, cyano, —CO$_2R^a$, —C(O)NR$^a$R$^b$, —SO$_2$NR$^a$R$^b$, aryl, or heteroaryl. In another embodiment, this invention relates to compounds of Formula (I), wherein $R^5$ is heterocycloalkyloxy- which is optionally substituted 1 or 2 times, independently, by halogen, hydroxyl, $(C_1-C_3)$alkoxy, amino, —NH$(C_1-C_3)$alkyl, —N$((C_1-C_3)$alkyl$)_2$, $(C_1-C_3)$alkyl, $(C_1-C_3)$alkoxy$(C_1-C_3)$alkyl-, amino$(C_1-C_3)$alkyl-, $((C_1-C_3)$alkyl)NH$(C_1-C_3)$alkyl-, $((C_1-C_3)$alkyl$)_2$N$(C_1-C_3)$alkyl-, $(C_3-C_8)$cycloalkyl, cyano, —CO$_2R^a$, —C(O)NR$^a$R$^b$, —SO$_2$NR$^a$R$^b$, phenyl, or heteroaryl.

In another embodiment, this invention relates to compounds of Formula (I), wherein $R^5$ is selected from the group consisting of cyclopentyloxy, cyclohexyloxy, pyrrolidinyloxy, piperidinyloxy, and tetrahydropyranyloxy, each of which is optionally substituted by hydroxyl, $(C_1-C_3)$alkoxy, amino, —NH$(C_1-C_3)$alkyl, —N$((C_1-C_3)$alkyl$)_2$, $(C_1-C_3)$alkyl, —CO$_2R^a$, —C(O)NR$^a$R$^b$, —SO$_2$NR$^a$R$^b$, phenyl, furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, or pyrimidinyl, wherein R$^a$ is $(C_1-C_4)$alkyl or phenyl$(C_1-C_2)$alkyl and R$^b$ is hydrogen or $(C_1-C_4)$alkyl.

In another embodiment, this invention relates to compounds of Formula (I), wherein $R^5$ is —NR$^a$R$^b$. In another embodiment, this invention relates to compounds of Formula (I), wherein $R^5$ is —NR$^a$R$^b$; R$^a$ is azetidinyl, oxetanyl, pyrrolidinyl, piperidinyl, piperazinyl, morpholinyl, thiomorpholinyl, or tetrahydropyranyl, each of which is optionally substituted 1 or 2 times, independently, by $(C_1-C_4)$alkyl; and R$^b$ is hydrogen or $(C_1-C_4)$alkyl. In another embodiment, this invention relates to compounds of Formula (I), wherein $R^5$ is —NR$^a$R$^b$; R$^a$ is azetidinyl, oxetanyl, pyrrolidinyl, piperidinyl, piperazinyl, morpholinyl, thiomorpholinyl, or tetrahydropyranyl; and R$^b$ is methyl or ethyl.

In another embodiment, this invention relates to compounds of Formula (I), wherein R$^5$ is —NR$^a$R$^b$; R$^a$ is cyclopentyl or cyclohexyl, each of which is optionally substituted by amino, —NH(C$_1$-C$_4$)alkyl, or —N((C$_1$-C$_4$)alkyl)$_2$; and R$^b$ is hydrogen or (C$_1$-C$_4$)alkyl. In another embodiment, this invention relates to compounds of Formula (I), wherein R$^5$ is —NR$^a$R$^b$; R$^a$ is cyclopentyl or cyclohexyl, each of which is optionally substituted by —N((C$_1$-C$_2$)alkyl)$_2$; and R$^b$ is methyl or ethyl.

In another embodiment, this invention relates to compounds of Formula (I), wherein R$^6$ is selected from the group consisting of hydrogen, —SO$_2$(C$_1$-C$_4$)alkyl, halogen, (C$_1$-C$_6$)alkyl, (C$_1$-C$_4$)alkoxy, phenyl, heteroaryl, and cyano, wherein said phenyl or heteroaryl group is optionally substituted 1 or 2 times, independently, by (C$_1$-C$_4$)alkoxy, —NR$^a$R$^b$, R$^a$R$^b$N(C$_1$-C$_4$)alkyl-, (C$_1$-C$_4$)alkylheterocycloalkyl-, halogen, (C$_1$-C$_4$)alkyl, (C$_3$-C$_8$)cycloalkyl, or heterocycloalkyl.

In another embodiment, this invention relates to compounds of Formula (I), wherein R$^6$ is selected from the group consisting of hydrogen, cyano, halogen, (C$_1$-C$_4$)alkoxy, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, phenyl, pyridinyl, pyridazinyl, pyrazinyl, pyrimidinyl, and triazinyl, wherein said furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, phenyl, pyridinyl, pyridazinyl, pyrazinyl, pyrimidinyl, or triazinyl is optionally substituted by (C$_1$-C$_4$)alkoxy, —NR$^a$R$^b$, R$^a$R$^b$N(C$_1$-C$_4$)alkyl-, (C$_1$-C$_4$)alkylheterocycloalkyl-, halogen, (C$_1$-C$_4$)alkyl, (C$_3$-C$_8$)cycloalkyl, or heterocycloalkyl.

In another embodiment, this invention relates to compounds of Formula (I), wherein R$^6$ is phenyl which is optionally substituted by —NR$^a$R$^b$ or R$^a$R$^b$N(C$_1$-C$_4$)alkyl-.

In another embodiment, this invention relates to compounds of Formula (I), wherein R$^6$ is pyridinyl which is optionally substituted by —NR$^a$R$^b$ or R$^a$R$^b$N(C$_1$-C$_4$)alkyl-.

In another embodiment, this invention relates to compounds of Formula (I), wherein R$^6$ is hydrogen, halogen, (C$_1$-C$_4$)alkyl, or (C$_1$-C$_4$)alkoxy. In another embodiment, this invention relates to compounds of Formula (I), wherein R$^6$ is hydrogen or halogen. In a specific embodiment, this invention relates to compounds of Formula (I), wherein R$^6$ is hydrogen, fluorine, chlorine, or bromine. In a specific embodiment, this invention relates to compounds of Formula (I), wherein R$^6$ is hydrogen or chlorine. In a more specific embodiment, this invention relates to compounds of Formula (I), wherein R$^6$ is chlorine. In another specific embodiment, this invention relates to compounds of Formula (I), wherein R$^6$ is hydrogen.

In another embodiment, this invention relates to compounds of Formula (I), wherein R$^7$ is selected from the group consisting of hydrogen, (C$_1$-C$_6$)alkyl, (C$_3$-C$_6$)cycloalkyl, phenyl, and heteroaryl, wherein said phenyl or heteroaryl group is optionally substituted 1 or 2 times, independently, by (C$_1$-C$_4$)alkoxy, —NR$^a$R$^b$, R$^a$R$^b$N(C$_1$-C$_4$)alkyl-, (C$_1$-C$_4$)alkylheterocycloalkyl-, halogen, (C$_1$-C$_4$)alkyl, (C$_3$-C$_8$)cycloalkyl, or heterocycloalkyl.

In another embodiment, this invention relates to compounds of Formula (I), wherein R$^7$ is hydrogen or (C$_1$-C$_4$)alkyl.

In another embodiment, this invention relates to compounds of Formula (I), wherein R$^7$ is selected from the group consisting of furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, phenyl, pyridinyl, pyridazinyl, pyrazinyl, pyrimidinyl, and triazinyl, wherein said furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, phenyl, pyridinyl, pyridazinyl, pyrazinyl, pyrimidinyl, or triazinyl is optionally substituted by (C$_1$-C$_4$)alkoxy, —NR$^a$R$^b$, R$^a$R$^b$N(C$_1$-C$_4$)alkyl-, (C$_1$-C$_4$)alkylheterocycloalkyl-, halogen, (C$_1$-C$_4$)alkyl, (C$_3$-C$_8$)cycloalkyl, or heterocycloalkyl.

In another embodiment, this invention relates to compounds of Formula (I), wherein R$^7$ is phenyl which is optionally substituted by —NR$^a$R$^b$ or R$^a$R$^b$N(C$_1$-C$_4$)alkyl-.

In another embodiment, this invention relates to compounds of Formula (I), wherein R$^7$ is pyridinyl which is optionally substituted by —NR$^a$R$^b$ or R$^a$RN(C$_1$-C$_4$)alkyl-.

In another embodiment, this invention relates to compounds of Formula (I), wherein R$^8$ is selected from the group consisting of (C$_4$-C$_6$)alkyl, (C$_4$-C$_6$)cycloalkyl, heterocycloalkyl, and phenyl, wherein said (C$_4$-C$_6$)alkyl, (C$_4$-C$_6$)cycloalkyl, heterocycloalkyl, or phenyl is optionally substituted 1 or 2 times, independently, by —OR$^a$, —NR$^a$R$^b$, —NHCO$_2$R$^a$, (C$_1$-C$_3$)alkyl, R$^a$R$^b$N(C$_1$-C$_3$)alkyl-, R$^a$O(C$_1$-C$_3$)alkyl-, —CO$_2$R$^a$, —C(O)NR$^a$R$^b$, or —SO$_2$NR$^a$R$^b$.

In a particular embodiment, this invention relates to compounds of Formula (I), wherein:

X is O, S, or NR$^7$;
Y is N or CR$^6$;
Z is CR$^5$;
R$^1$ and R$^2$ are each independently (C$_1$-C$_4$)alkyl;
R$^3$ is hydrogen;
R$^4$ is methyl or chlorine;
R$^5$ is selected from the group consisting of (C$_3$-C$_6$)alkoxy, (C$_3$-C$_8$)cycloalkyloxy-, and heterocycloalkyloxy-, each of which is optionally substituted by hydroxyl, (C$_1$-C$_3$)alkoxy, amino, —NH(C$_1$-C$_3$)alkyl, —N((C$_1$-C$_3$)alkyl)$_2$, (C$_1$-C$_3$)alkyl, —CO$_2$R$^a$, —C(O)NR$^a$R$^b$, —SO$_2$NR$^a$R$^b$, phenyl, or heteroaryl;
R$^6$ is hydrogen, halogen, (C$_1$-C$_4$)alkyl, or (C$_1$-C$_4$)alkoxy; and
R$^7$ is hydrogen or (C$_1$-C$_4$)alkyl;
or pharmaceutically acceptable salts thereof.

In another particular embodiment, this invention relates to compounds of Formula (I), wherein:

X is O, S, or NR$^7$;
Y is N or CR$^6$;
Z is CR$^5$;
R$^1$ and R$^2$ are each independently (C$_1$-C$_4$)alkyl;
R$^3$ is hydrogen;
R$^4$ is methyl or chlorine;
R$^5$ is —NR$^a$R$^b$;
R$^6$ is hydrogen, halogen, (C$_1$-C$_4$)alkyl, or (C$_1$-C$_4$)alkoxy; and
R$^7$ is hydrogen or (C$_1$-C$_4$)alkyl;
or pharmaceutically acceptable salts thereof.

In another particular embodiment, this invention relates to compounds of Formula (I), wherein:

X is N or CR$^6$;
Y is O, S, or NR$^7$;
Z is CR$^5$;
R$^1$ and R$^2$ are each independently (C$_1$-C$_4$)alkyl;
R$^3$ is hydrogen;
R$^4$ is methyl or chlorine;
R$^5$ is selected from the group consisting of (C$_3$-C$_6$)alkoxy, (C$_3$-C$_8$)cycloalkyloxy-, and heterocycloalkyloxy-, each of which is optionally substituted by hydroxyl, (C$_1$-C$_3$)alkoxy, amino, —NH($C_1$-$C_3$)alkyl, —N(($C_1$-$C_3$)alkyl)$_2$, ($C_1$-$C_3$) alkyl, —$CO_2R^a$, —C(O)$NR^aR^b$, —$SO_2NR^aR^b$, phenyl, or heteroaryl;

$R^6$ is hydrogen, halogen, ($C_1$-$C_4$)alkyl, or ($C_1$-$C_4$)alkoxy; and $R^7$ is hydrogen or ($C_1$-$C_4$)alkyl;

or pharmaceutically acceptable salts thereof.

In another particular embodiment, this invention relates to compounds of Formula (I), wherein:

X is N or $CR^6$;
Y is O, S, or $NR^7$;
Z is $CR^5$;
$R^1$ and $R^2$ are each independently ($C_1$-$C_4$)alkyl;
$R^3$ is hydrogen;
$R^4$ is methyl or chlorine;
$R^5$ is —$NR^aR^b$;
$R^6$ is hydrogen, halogen, ($C_1$-$C_4$)alkyl, or ($C_1$-$C_4$)alkoxy; and
$R^7$ is hydrogen or ($C_1$-$C_4$)alkyl;

or pharmaceutically acceptable salts thereof.

In another embodiment, this invention also relates to compounds of Formula (II):

(II)

or pharmaceutically acceptable salts thereof, wherein X is O, S, or $NR^7$; Y is N or $CR^6$; and $R^1$, $R^2$, $R^3$, $R^4$, $R^5$, $R^6$, and $R^7$ are defined according to Formula (I). In another embodiment, this invention relates to compounds of Formula (II), wherein X is O or S and Y is N or $CR^6$. In another embodiment, this invention relates to compounds of Formula (II), wherein X is O or S and Y is $CR^6$. In another embodiment, this invention relates to compounds of Formula (II), wherein X is O or S and Y is N. In another embodiment, this invention relates to compounds of Formula (II), wherein X is S and Y is $CR^6$.

In another embodiment, this invention also relates to compounds of Formula (II)(a):

(II)(a)

or pharmaceutically acceptable salts thereof, wherein $R^1$, $R^2$, $R^3$, $R^4$, $R^5$, and $R^6$ are defined according to Formula (I).

In another embodiment, this invention also relates to compounds of Formula (III):

(III)

or pharmaceutically acceptable salts thereof, wherein Y is O, S, or $NR^7$; X is N or $CR^6$; and $R^1$, $R^2$, $R^3$, $R^4$, $R^5$, $R^6$, and $R^7$ are defined according to Formula (I). In another embodiment, this invention relates to compounds of Formula (III), wherein Y is O or S and X is N or $CR^6$. In another embodiment, this invention relates to compounds of Formula (III), wherein Y is O or S and X is $CR^6$. In another embodiment, this invention relates to compounds of Formula (III), wherein Y is O or S and X is N. In another embodiment, this invention relates to compounds of Formula (III), wherein Y is S and X is $CR^6$.

In another embodiment, this invention also relates to compounds of Formula (III)(a):

(III)(a)

or pharmaceutically acceptable salts thereof, wherein $R^1$, $R^2$, $R^3$, $R^4$, $R^5$, and $R^6$ are defined according to Formula (I).

In another embodiment, this invention also relates to compounds of Formula (IV):

(IV)

or pharmaceutically acceptable salts thereof, wherein X is N or $CR^6$; Y is N or $CR^6$; and $R^1$, $R^2$, $R^3$, $R^4$, $R^6$, and $R^8$ are defined according to Formula (I). In another embodiment, this invention relates to compounds of Formula (IV), wherein X is N and Y is $CR^6$. In another embodiment, this invention relates to compounds of Formula (IV), wherein X is $CR^6$ and Y is N. In another embodiment, this invention relates to compounds of Formula (IV), wherein X and Y are each independently $CR^6$. In another embodiment, this invention relates to compounds of Formula (IV), wherein X and Y are each N.

Specific compounds of this invention include:
N-((2,6-dimethyl-4-oxo-1,4-dihydropyridin-3-yl)methyl)-5-(ethyl(tetrahydro-2H-pyran-4-yl)amino)-4-methylthiophene-3-carboxamide;
N-((2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide;
N-((5-amino-2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide; and
2-bromo-N-((2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide;
or pharmaceutically acceptable salts thereof.

Typically, but not absolutely, the salts of the present invention are pharmaceutically acceptable salts. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labeled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulfur, fluorine, chlorine, and iodine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent.

The invention further provides a pharmaceutical composition (also referred to as pharmaceutical formulation) comprising a compound of Formula (I) or pharmaceutically acceptable salt thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Pharmaceutical compositions may be in unit dose form containing a predetermined amount of active ingredient per unit dose. Such a unit may contain a therapeutically effective dose of the compound of Formula (I) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

In accordance with another aspect of the invention there is provided a process for the preparation of a pharmaceutical composition comprising mixing (or admixing) a compound of Formula (I) or salt thereof with at least one excipient.

The present invention also provides a method of treatment in a mammal, especially a human. The compounds and compositions of the invention are used to treat cellular proliferation diseases. Disease states which can be treated by the methods and compositions provided herein include, but are not limited to, cancer (further discussed below), autoimmune disease, fungal disorders, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still requires treatment. For example, during wound healing, the cells may be proliferating "normally", but proliferation enhancement may be desired. Thus, in one embodiment, the invention herein includes application to cells or individuals afflicted or impending affliction with any one of these disorders or states.

The compositions and methods provided herein are particularly deemed useful for the treatment of cancer including tumors such as prostate, breast, brain, skin, cervical carcinomas, testicular carcinomas, etc. They are particularly useful in treating metastatic or malignant tumors. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one or related of the above identified conditions.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the EZH2 inhibitors of this disclosure are not in and of themselves active or significantly active, but when combined with another therapy, which may or may not be active as a standalone therapy, the combination provides a useful therapeutic outcome.

By the term "co-administering" and derivatives thereof as used herein refers to either simultaneous administration or any manner of separate sequential administration of an EZH2 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of specified cancers in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical antineoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; DNA methyltransferase inhibitors such as azacitidine and decitabine; signal transduction pathway inhibitors; non-receptor tyrosine kinase angiogenesis inhibitors; immunotherapeutic agents; proapoptotic agents; and cell cycle signaling inhibitors.

Typically, any chemotherapeutic agent that has activity against a susceptible neoplasm being treated may be utilized in combination with the compounds the invention, provided that the particular agent is clinically compatible with therapy employing a compound of the invention. Typical antineoplastic agents useful in the present invention include, but are not limited to: alkylating agents, anti-metabolites, antitumor antibiotics, antimitotic agents, nucleoside analogues, topoisomerase I and II inhibitors, hormones and hormonal analogues; retinoids, histone deacetylase inhibitors; signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Nucleoside analogues are those compounds which are converted to deoxynucleotide triphosphates and incorporated into replicating DNA in place of cytosine. DNA methyltransferases become covalently bound to the modified bases resulting in an inactive enzyme and reduced DNA methylation. Examples of nucleoside analogues include azacitidine and decitabine which are used for the treatment of myelodysplastic disorder. Histone deacetylase (HDAC) inhibitors include vorinostat, for the treatment of cutaneous T-cell lymphoma. HDACs modify chromatin through the deacetylation of histones. In addition, they have a variety of substrates including numerous transcription factors and signaling molecules. Other HDAC inhibitors are in development.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha, beta$_3$) that inhibit angiogenesis; endostatin and angiostatin (non-RTK) may also prove useful in combination with the compounds of the invention. One example of a VEGFR antibody is bevacizumab (AVASTIN®)).

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb) and erlotinib (TARCEVA®). Imatinib mesylate (GLEEVEC) is one example of a PDGFR inhibitor. Examples of VEGFR inhibitors include pazopanib (Votrient®), ZD6474, AZD2171, PTK787, sunitinib and sorafenib.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem. Soc., 93:2325 (1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Int. Med., 111:273, 1989) and for the treatment of breast cancer (Holmes et al., J. Nat. Cancer Inst., 83:1797, 1991.). It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S, 10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leukopenialeukopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leukopenialeukopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leukopenialeukopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leukopenialeukopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2', 2'-difluorocytidine monohydrochloride ((3-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leukopenialeukopenia, thrombocytopenia, and anemia, is the most common dose limiting side effect of gemcitabine administration.

Methotrexate, N-[4[[(2,4-diamino-6-pteridinyl)methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leukopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the Formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of Formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavoring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of Formula (I) for the treatment of anemia will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of Formula (I) per se. It is envisaged that similar dosages would be appropriate for treatment of the other conditions referred to above.

DEFINITIONS

Terms are used within their accepted meanings. The following definitions are meant to clarify, but not limit, the terms defined.

As used herein, the term "alkyl" represents a saturated, straight or branched hydrocarbon moiety having the specified number of carbon atoms. The term "$(C_1-C_6)$alkyl" refers to an alkyl moiety containing from 1 to 6 carbon atoms. Exemplary alkyls include, but are not limited to methyl, ethyl, n-propyl, isopropyl, n-butyl, isobutyl, s-butyl, t-butyl, pentyl, and hexyl.

When the term "alkyl" is used in combination with other substituent groups, such as "halo$(C_1-C_4)$alkyl", "hydroxy$(C_1-C_4)$alkyl" or "aryl$(C_1-C_4)$alkyl-", the term "alkyl" is intended to encompass a divalent straight or branched-chain hydrocarbon radical, wherein the point of attachment is through the alkyl moiety. The term "halo$(C_1-C_4)$alkyl" is intended to mean a radical having one or more halogen atoms, which may be the same or different, at one or more carbon atoms of an alkyl moiety containing from 1 to 4 carbon atoms, which is a straight or branched-chain carbon radical. Examples of "halo$(C_1-C_4)$alkyl" groups useful in the present invention include, but are not limited to, —$CF_3$ (trifluoromethyl), —$CCl_3$ (trichloromethyl), 1,1-difluoroethyl, 2,2,2-trifluoroethyl, and hexafluoroisopropyl. Examples of "aryl$(C_1-C_4)$alkyl-" groups useful in the present invention include, but are not limited to, benzyl (phenylmethyl), 1-methylbenzyl (1-phenylethyl), 1,1-dimethylbenzyl (1-phenylisopropyl), and phenethyl (2-phenylethyl). Examples of "hydroxy$(C_1-C_4)$alkyl" groups useful in the present invention include, but are not limited to, hydroxymethyl, hydroxyethyl, and hydroxyisopropyl.

"Alkoxy" refers to a group containing an alkyl radical, defined hereinabove, attached through an oxygen linking atom. The term "$(C_1-C_4)$alkoxy" refers to a straight- or branched-chain hydrocarbon radical having at least 1 and up to 4 carbon atoms attached through an oxygen linking atom. Exemplary "$(C_1-C_4)$alkoxy" groups useful in the present invention include, but are not limited to, methoxy, ethoxy, n-propoxy, isopropoxy, n-butoxy, s-butoxy, isobutoxy, and t-butoxy.

When "cycloalkyl" is used it refers to a non-aromatic, saturated, cyclic hydrocarbon ring containing the specified number of carbon atoms. So, for example, the term "$(C_3-C_8)$cycloalkyl" refers to a non-aromatic cyclic hydrocarbon ring having from three to eight carbon atoms. Exemplary "$(C_3-C_8)$cycloalkyl" groups useful in the present invention include, but are not limited to, cyclopropyl, cyclobutyl, cyclopentyl, cyclohexyl, cycloheptyl, and cyclooctyl.

As used herein, the term "cycloalkyloxy-" refers to a group containing a cycloalkyl radical, defined hereinabove, attached through an oxygen linking atom. Exemplary "$(C_3-C_8)$cycloalkyloxy-" groups useful in the present invention include cyclopropyloxy, cyclobutyloxy, cyclopentyloxy, cyclohexyloxy, cycloheptyloxy, and cyclooctyloxy.

As used herein, the term "bicycloalkyl" refers to a saturated, bridged, fused, or spiro, bicyclic hydrocarbon ring system containing the specified number of carbon atoms. Exemplary "($C_6$-$C_{10}$)bicycloalkyl" groups include, but are not limited to bicyclo[2.1.1]hexyl, bicyclo[2.1.1]heptyl, bicyclo[3.2.1]octyl, bicyclo[2.2.2]octyl, bicyclo[3.2.2]nonyl, bicyclo[3.3.1]nonyl, bicyclo[3.3.2]decyl, bicyclo[4.3.1]decyl, bicyclo[2.2.0]hexyl, bicyclo[3.1.0]hexyl, bicyclo[3.2.0]heptyl, bicyclo[4.1.0]heptyl, octahydropentalenyl, bicyclo[4.2.0]octyl, decahydronaphthalenyl, spiro[3.3]heptyl, spiro[2.4]heptyl, spiro[3.4]octyl, spiro[2.5]octyl, spiro[4.4]nonyl, spiro[3.5]nonyl, and spiro[4.5]decyl.

The terms "halogen" and "halo" represent chloro, fluoro, bromo, or iodo substituents. "Hydroxy" or "hydroxyl" is intended to mean the radical —OH.

"Heterocycloalkyl" represents a group or moiety comprising a non-aromatic, monovalent monocyclic or bicyclic radical, which is saturated or partially unsaturated, containing 3 to 10 ring atoms, which includes 1 to 3 heteroatoms independently selected from nitrogen, oxygen and sulfur, including N-oxides, sulfur oxides, and dioxides. Illustrative examples of heterocycloalkyls useful in the present invention include, but are not limited to, aziridinyl, azetidinyl, pyrrolidinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, morpholinyl, thiomorpholinyl, tetrahydropyranyl, dihydropyranyl, 1,3-dioxanyl, 1,4-dioxanyl, 1,3-oxathiolanyl, 1,3-oxathianyl, 1,3-dithianyl, 1,4-dithianyl, hexahydro-1H-1,4-diazepinyl, azabicyclo[3.2.1]octyl, azabicyclo[3.3.1]nonyl, azabicylo[4.3.0]nonyl, oxabicylo[2.2.1]heptyl, 1,1-dioxidotetrahydro-2H-thiopyranyl, and 1,5,9-triazacyclododecyl.

As used herein, the term "heterocycloalkyloxy-" refers to a group containing a heterocycloalkyl radical, defined hereinabove, attached through an oxygen linking atom. Illustrative examples of heterocycloalkyloxy groups useful in the present invention include, but are not limited to, aziridinyloxy, azetidinyloxy, pyrrolidinyloxy, pyrazolidinyloxy, pyrazolinyloxy, imidazolidinyloxy, imidazolinyloxy, oxazolinyloxy, thiazolinyloxy, tetrahydrofuranyloxy, dihydrofuranyloxy, 1,3-dioxolanyloxy, piperidinyloxy, piperazinyloxy, morpholinyloxy, thiomorpholinyloxy, tetrahydropyranyloxy, dihydropyranyloxy, 1,3-dioxanyloxy, 1,4-dioxanyloxy, 1,3-oxathiolanyloxy, 1,3-oxathianyloxy, 1,3-dithianyloxy, hexahydro-1H-1,4-diazepinyloxy, azabicyclo[3.2.1]octyloxy, azabicyclo[3.3.1]nonyloxy, azabicyclo[4.3.0]nonyloxy, oxabicylo[2.2.1]heptyloxy, 1,1-dioxidotetrahydro-2H-thiopyranyloxy, and 1,5,9-triazacyclododecyloxy.

The term "aryl" refers to a monocyclic or fused bicyclic groups having 6 to 14 carbon atoms and having at least one aromatic ring that complies with Hückel's Rule. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl.

As used herein, the term "heteroaryl" refers to an aromatic ring system containing carbon(s) and at least one heteroatom selected from nitrogen, oxygen and sulfur, including N-oxides. Heteroaryl may be monocyclic or polycyclic, substituted or unsubstituted. A monocyclic heteroaryl group may have 1 to 4 heteroatoms in the ring, while a polycyclic heteroaryl may contain 1 to 8 heteroatoms. Bicyclic heteroaryl rings may contain from 8 to 10 member atoms. Monocyclic heteroaryl rings may contain from 5 to 6 member atoms (carbons and heteroatoms). Exemplary 5- to 6-membered heteroaryls include, but are not limited to, furanyl, thiophenyl, thienyl, pyrrolyl, imidazolyl, pyrazolyl, triazolyl, tetrazolyl, thiazolyl, isothiazolyl, 1,2,3-triazolyl, 1,2,4-triazolyl, oxazolyl, isoxazolyl, 1,2,3-oxadiazolyl, 1,2,5-oxadiazolyl, thiadiazolyl, isothiazolyl, tetrazolyl, pyridinyl, pyridazinyl, pyrazinyl, pyrimidinyl, and triazinyl. Other exemplary heteroaryl groups include, but are not limited to benzofuranyl, isobenzofuryl, 2,3-dihydrobenzofuryl, 1,3-benzodioxolyl, dihydrobenzodioxinyl, benzothienyl, indolizinyl, indolyl, isoindolyl, indolinyl, isoindolinyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, pyrrolopyridinyl, pyrrolopyrimidinyl, imidazopyridinyl, imidazopyrimidinyl, pyrazolopyridinyl, pyrazolopyrimidinyl, benzoxadiazolyl, benzthiadiazolyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

As used herein, the term "cyano" refers to the group —CN.

As used herein, the term "optionally" means that the subsequently described event(s) may or may not occur, and includes both event(s) that occur and event(s) that do not occur.

As used herein, unless otherwise defined, the phrase "optionally substituted" or variations thereof denote an optional substitution, including multiple degrees of substitution, with one or more substituent group. The phrase should not be interpreted as duplicative of the substitutions herein described and depicted.

As used herein, the term "treatment" refers to alleviating the specified condition, eliminating or reducing one or more symptoms of the condition, slowing or eliminating the progression of the condition, and preventing or delaying the reoccurrence of the condition in a previously afflicted or diagnosed patient or subject.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I), as well as salts thereof, may be administered as the raw chemical. Additionally, the active ingredient may be presented as a pharmaceutical composition.

Compound Preparation

Abbreviations $Boc_2O$ di-tert-butyl dicarbonate
$CaCl_2$ calcium (II) chloride

CH₃Cl chloroform
CH₃CN acetonitrile
DCE 1,2-dichloroethane
DCM dichloromethane
DMAP 4-dimethylaminopyridine
DMF N,N-dimethylformamide
DMSO dimethylsulfoxide
EtOAc ethyl acetate
EDC N-(3-dimethylaminopropyl)-N'-ethylcarbodiimide hydrochloride
ES electrospray
Et₂O diethyl ether
EtOAc ethyl acetate
EtOH ethanol
h hour(s)
HCl hydrochloric acid
H₂O water
HOAt 1-hydroxy-7-azabenzotriazole
HOBt 1-hydroxybenzotriazole
HPLC high-performance liquid chromatography
LCMS liquid chromatography mass spectrometry
MeOH methanol
MgCl₂ magnesium chloride
MgSO₄ magnesium sulfate
min minute(s)
MS mass spectrometry
NaBH₄ sodium borohydride
NaBH(OAc)₃ sodium triacetoxyborohydride
Na₂CO₃ sodium carbonate
NaHCO₃ sodium bicarbonate
NaOH sodium hydroxide
Na₂S₂O₃ sodium thiosulfate
NBS N-bromosuccinimide
NH₃ ammonia
NH₄Cl ammonium chloride
NH₄OH ammonium hydroxide
NIS N-iodosuccinimide
NMM N-methylmorpholine
PyBroP® bromotripyrrolidinophosphonium hexafluorophosphate
sat. saturated
TBME tert-butyl methyl ether
THF tetrahydrofuran
TFA trifluoroacetic acid Generic Synthesis Schemes The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention. Starting materials are commercially available or are made from commercially available starting materials using methods known to those skilled in the art.

The compounds of Formula (I) can be prepared according to Scheme 1 or analogous methods. An appropriately substituted 3-aminoacrylonitrile is condensed with an appropriately substituted 1,3-dioxin-4-one with heating to produce a 1,4-dihydropyridin-4-one. Reduction of the nitrile under the appropriate conditions, such as with a Raney nickel catalyst in a hydrogen atmosphere, followed by coupling of the resultant amine with an appropriately substituted carboxylic acid affords compounds of Formula (I).

Scheme 1: Synthesis of Compounds of Formula (I).

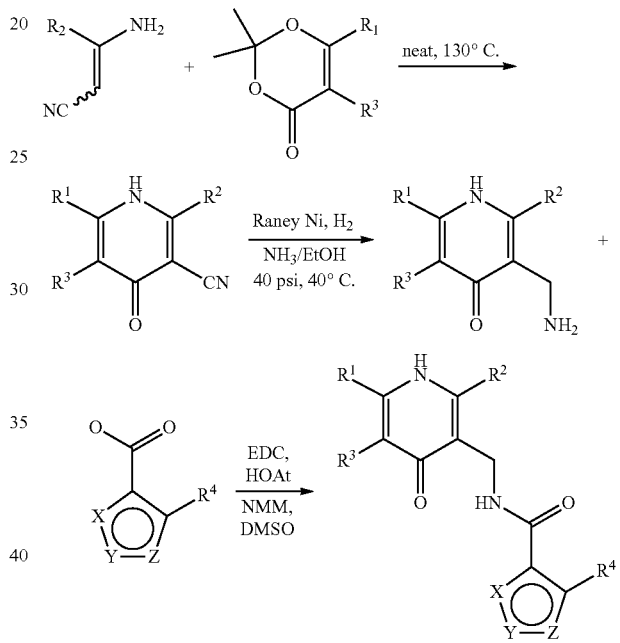

The compounds of Formula (I) can also be prepared according to Scheme 2 or analogous methods. Successive reductive alkylations of an appropriately substituted 5-amino-thiophene-3-carboxylate (or its regioisomer) with appropriately substituted aldehydes or ketones furnishes the substituted amines. Saponification of the ester, followed by coupling of the resultant carboxylic acid with an appropriately substituted amine affords compounds of Formula (I).

Scheme 2: Synthesis of Compounds of Formula (I).

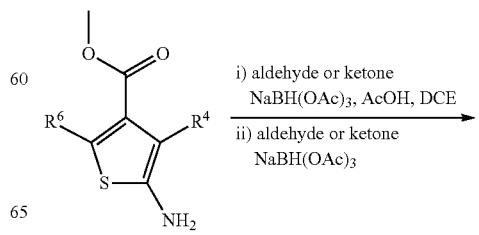

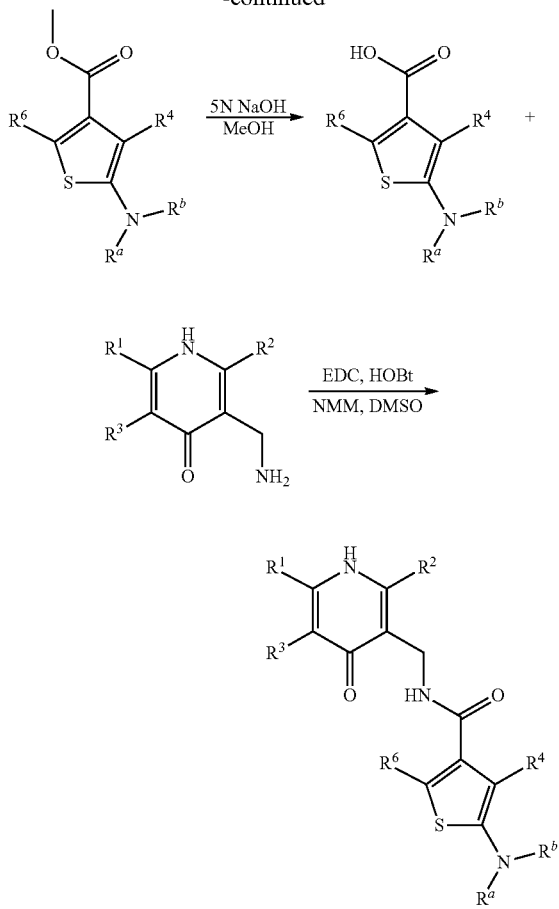

EXPERIMENTALS

The following guidelines apply to all experimental procedures described herein. All reactions were conducted under a positive pressure of nitrogen using oven-dried glassware, unless otherwise indicated. Temperatures designated are external (i.e. bath temperatures), and are approximate. Air and moisture-sensitive liquids were transferred via syringe. Reagents were used as received. Solvents utilized were those listed as "anhydrous" by vendors. Molarities listed for reagents in solutions are approximate, and were used without prior titration against a corresponding standard. All reactions were agitated by stir bar, unless otherwise indicated. Heating was conducted using heating baths containing silicon oil, unless otherwise indicated. Reactions conducted by microwave irradiation (0-400 W at 2.45 GHz) were done so using a Biotage Initiator™ 2.0 instrument with Biotage microwave EXP vials (0.2-20 mL) and septa and caps. Irradiation levels utilized (i.e. high, normal, low) based on solvent and ionic charge were based on vendor specifications. Cooling to temperatures below −70° C. was conducted using dry ice/acetone or dry ice/2-propanol. Magnesium sulfate and sodium sulfate used as drying agents were of anhydrous grade, and were used interchangeably. Solvents described as being removed "in vacuo" or "under reduced pressure" were done so by rotary evaporation.

Preparative normal phase silica gel chromatography was carried out using either a Teledyne ISCO CombiFlash Companion instrument with RediSep or ISCO Gold silica gel cartridges (4 g-330 g), or an Analogix IF280 instrument with SF25 silica gel cartridges (4 g-3-00 g), or a Biotage SP1 instrument with HP silica gel cartridges (10 g-100 g). Purification by reverse phase HPLC was conducted using a YMC-pack column (ODS-A 75×30 mm) as solid phase, unless otherwise noted. A mobile phase of 25 mL/min A ($CH_3CN$-0.1% TFA): B (water-0.1% TFA), 10-80% gradient A (10 min) was utilized with UV detection at 214 nM, unless otherwise noted.

A PE Sciex API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, Mass., USA) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

Method A LCMS. Samples were introduced into the mass spectrometer using a CTC PAL autosampler (LEAP Technologies, Carrboro, N.C.) equipped with a hamilton 10 uL syringe which performed the injection into a Valco 10-port injection valve. The HPLC pump was a Shimadzu LC-10ADvp (Shimadzu Scientific Instruments, Columbia, Md.) operated at 0.3 mL/min and a linear gradient 4.5% A to 90% B in 3.2 min. with a 0.4 min. hold. The mobile phase was composed of 100% ($H_2O$ 0.02% TFA) in vessel A and 100% ($CH_3CN$ 0.018% TFA) in vessel B. The stationary phase is Aquasil (C18) and the column dimensions were 1 mm×40 mm. Detection was by UV at 214 nm, evaporative light-scattering (ELSD) and MS.

Method B, LCMS. Alternatively, an Agilent 1100 analytical HPLC system with an LC/MS was used and operated at 1 mL/min and a linear gradient 5% A to 100% B in 2.2 min with a 0.4 min hold. The mobile phase was composed of 100% ($H_2O$ 0.02% TFA) in vessel A and 100% ($CH_3CN$ 0.018% TFA) in vessel B. The stationary phase was Zobax (C8) with a 3.5 um particle size and the column dimensions were 2.1 mm×50 mm. Detection was by UV at 214 nm, evaporative light-scattering (ELSD) and MS.

Method C, LCMS. Alternatively, an MDSSCIEX API 2000 equipped with a capillary column of (50×4.6 mm, 5 μm) was used. HPLC was done on Agilent-1200 series UPLC system equipped with column Zorbax SB-$C_{18}$ (50× 4.6 mm, 1.8 μm) eluting with $CH_3CN$: ammonium acetate buffer. The reactions were performed in the microwave (CEM, Discover).

$^1$H-NMR spectra were recorded at 400 MHz using a Bruker AVANCE 400 MHz instrument, with ACD Spect manager v. 10 used for reprocessing. Multiplicities indicated are: s=singlet, d=doublet, t=triplet, q=quartet, quint=quintet, sxt=sextet, m=multiplet, dd=doublet of doublets, dt=doublet of triplets etc. and br indicates a broad signal. All NMRs in DMSO-$d_6$ unless otherwise noted.

Analytical HPLC: Products were analyzed by Agilent 1100 Analytical Chromatography system, with 4.5×75 mm Zorbax XDB-$C_{18}$ column (3.5 um) at 2 mL/min with a 4 min gradient from 5% $CH_3CN$ (0.1% formic acid) to 95% $CH_3CN$ (0.1% formic acid) in $H_2O$ (0.1% formic acid) and a 1 min hold.

Intermediates

Intermediate 1

3-(Aminomethyl)-2,6-dimethylpyridin-4(1H)-one hydrochloride

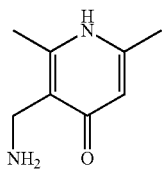

a) 2,6-Dimethyl-4-oxo-1,4-dihydropyridine-3-carbonitrile

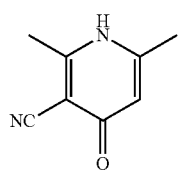

A 250 mL round bottom flask was charged with 3-aminobut-2-enenitrile (10.00 g, 122 mmol), 2,2,6-trimethyl-4H-1,3-dioxin-4-one (32.4 mL, 244 mmol), and a magnetic stir bar. The flask was equipped with a reflux condenser and a CaCl$_2$ tube and the reaction mixture was heated at 130° C. for 1 h. The reaction was allowed to cool room temperature and was diluted with EtOAc (100 mL). The solid that formed was collected, washed with EtOAc (20 mL), and dried to give 2,6-dimethyl-4-oxo-1,4-dihydropyridine-3-carbonitrile (3.5 g, 19.4%) as a beige solid. $^1$H-NMR (400 MHz, DMSO-d$_6$) δ11.94 (br. s., 1H), 6.04 (s, 1H), 2.41 (s, 3H), 2.21 (s, 3H). MS(ES) [M+H]$^+$ 148.9.

b) 3-(Aminomethyl)-2,6-dimethylpyridin-4(1H)-one hydrochloride

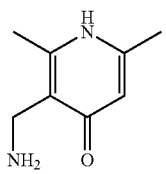

A 250 mL Erlenmeyer flask was charged with 2,6-dimethyl-4-oxo-1,4-dihydropyridine-3-carbonitrile (360 mg, 2.430 mmol) and cold 2 M NH$_3$ in EtOH (39.5 mL, 79 mmol). EtOH (40 mL) was added to solubilize the remaining reactant. The solution was passed through a Raney Ni cartridge on a continuous flow hydrogenation reactor (40 psi, 40° C., 1 mL/min) for 16 h. The reaction solvent was removed in vacuo and the residue was dissolved in EtOH (1 mL) and CHCl$_3$ (15 mL), then concentrated in vacuo. The residue was dissolved and concentrated in CHCl$_3$ (2×15 mL) and DCM (15 mL). The sticky residue was suspended in Et$_2$O (30 mL) and treated with 4 M HCl in 1,4-dioxanes (10.63 mL, 42.5 mmol). The suspension was stirred at room temperature overnight, after which time the white solid was collected via vacuum filtration, washed with Et$_2$O (10 mL), and dried under high vacuum to give 3-(aminomethyl)-2,6-dimethylpyridin-4(1H)-one hydrochloride (200 mg, 80%) as a white solid. $^1$H NMR (400 MHz, CDCl$_3$) δ 6.26 (br. s., 1H), 3.90 (br. s., 2H), 2.64 (s, 1H), 2.38 (s, 3H), 2.32 (s, 3H), 1.22-1.30 (m, 2H). MS(ES) [M+H]$^+$ 152.9.

Intermediate 2

3-Amino-5-(aminomethyl)-2,6-dimethylpyridin-4 (1H)-one

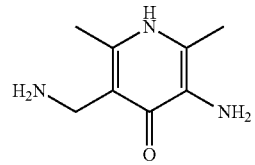

a) 2,6-Dimethyl-3-nitropyridin-4(1H)-one

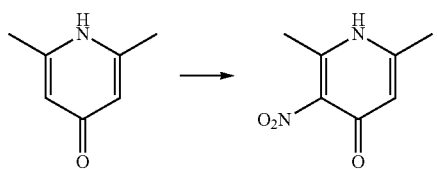

To a cooled (0° C.) solution of sulfuric acid (4.0 mL, 16.24 mmol) was added nitric acid (fuming) (4.0 mL, 16.24 mmol) slowly over 5 min. The mixture was stirred for 30 min, at which time was added 2,6-dimethylpyridin-4(1H)-one (2.0 g, 16.24 mmol) in portions over 5 min. The reaction was allowed to warm to ambient temperature and then heated at 100° C. for 2 h, at which time it was allowed to cool back to ambient temperature. The reaction was poured onto ice (33 g) and the mixture was cooled in an ice bath. 8 M NaOH was added and the pH adjusted to 5.3. The solids were filtered and collected to provide 2,6-dimethyl-3-nitropyridin-4(1H)-one (440 mg, 15.79%). $^1$H NMR (DMSO-d6) δ 11.84 (br. s., 1H), 6.18 (s, 1H), 2.28 (s, 3H), 2.22 (s, 3H). MS(ES) [M+H]$^+$ 168.99.

b) 3-Iodo-2,6-dimethyl-5-nitropyridin-4(1H)-one

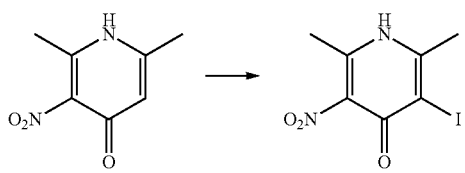

To a mixture 2,6-dimethyl-3-nitropyridin-4(1H)-one (0.44 g, 2.62 mmol) in acetic acid (13 mL) was NIS (0.765 g, 3.40 mmol). The reaction was heated at 105° C. for 2 h.

The reaction was then quenched with ice/water (100 mL) and 0.1 M Na₂S₂O₃ (2 mL) was added. The solids were filtered and collected to provide 3-iodo-2,6-dimethyl-5-nitropyridin-4(1H)-one (596 mg, 69.7%). ¹H NMR (DMSO-d6) δ 12.32 (br. s., 1H), 2.28-2.31 (m, 3H). MS(ES) [M+H]⁺ 294.9.

c) 2,6-Dimethyl-5-nitro-4-oxo-1,4-dihydropyridine-3-carbonitrile

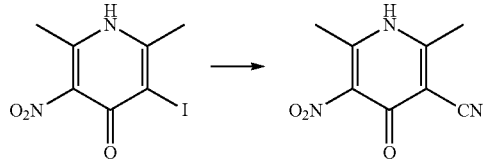

A mixture of 3-iodo-2,6-dimethyl-5-nitropyridin-4(1H)-one (0.59 g, 2.006 mmol) and copper(I) cyanide (0.359 g, 4.01 mmol) in N-methyl-2-pyrrolidone (10 mL) was heated at 125° C. for 2 h. The reaction was then quenched with ice/sat. NH₄Cl (100 mL) and cooled in an ice bath for 1 h. The solids were filtered and collected to provide 2,6-dimethyl-5-nitro-4-oxo-1,4-dihydropyridine-3-carbonitrile (176 mg, 40.9%). ¹H NMR (DMSO-d6) δ 12.78 (br. s., 1H), 2.44-2.48 (m, 3H), 2.30-2.38 (m, 3H). MS(ES) [M+H]⁺ 193.9.

d) 1,1-Dimethylethyl {[5-({[(1,1-dimethylethyl)oxy]carbonyl}amino)-2,6-dimethyl-4-oxo-1,4-dihydro-3-pyridinyl]methyl}carbamate

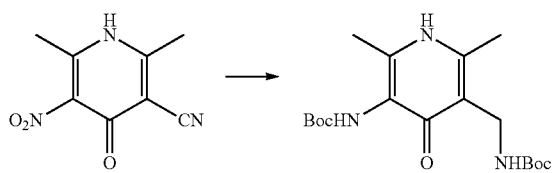 [SMILES: Cc1[nH]c(C)c([N+](=O)[O-])c(=O)c1C#N ; Cc1[nH]c(C)c(NC(=O)OC(C)(C)C)c(=O)c1CNC(=O)OC(C)(C)C]

To a cooled (0° C.) solution of 2,6-dimethyl-5-nitro-4-oxo-1,4-dihydropyridine-3-carbonitrile (1.6 g, 6.21 mmol) in MeOH (60 mL) were added Boc₂O (4.33 mL, 18.64 mmol) and nickel chloride-hexahydrate (0.738 g, 3.11 mmol), followed by NaBH₄ (2.350 g, 62.1 mmol) slowly over about 2 min. The reaction was stirred for 10 min at 0° C., then was stirred at ambient temperature overnight. To the mixture was added diethylenetriamine (2.70 mL, 24.85 mmol). The reaction was stirred for 1 h, at which time it was quenched with sat. NaHCO₃, extracted with 4:1 EtOAc/THF, and concentrated. The residue was dissolved in MeOH/DCM, adsorbed onto silica gel, and purified by column chromatography (12 g silica column; Gradient of B: 10-85%, A: DCM, B: 10% MeOH in DCM) to provide 1,1-dimethylethyl {[5-({[(1,1-dimethyl ethyl)oxy]carbonyl}amino)-2,6-dimethyl-4-oxo-1,4-dihydro-3-pyridinyl]methyl}carbamate (880 mg, 38.6%). ¹H NMR (DMSO-d6) δ 11.08 (s, 1H), 7.57 (br. s., 1H), 6.45 (t, J=5.1 Hz, 1H), 3.94 (d, J=5.3 Hz, 2H), 2.24-2.33 (m, 2H), 2.08-2.16 (m, 4H), 1.40 (s, 12H), 1.33-1.37 (m, 7H). MS(ES) [M+H]⁺ 368.2.

e) 3-Amino-5-(aminomethyl)-2,6-dimethylpyridin-4(1H)-one bis-hydrochloride

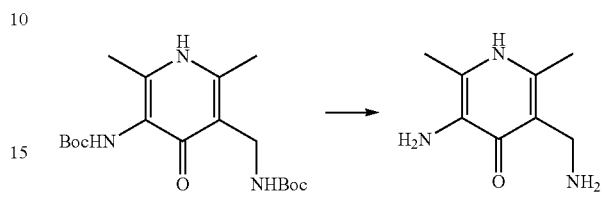

To a solution of 4 M HCl/dioxane (10.18 mL, 40.7 mmol) was added slowly a solution of 1,1-dimethylethyl {[5-({[(1,1-dimethylethyl)oxy]carbonyl}amino)-2,6-dimethyl-4-oxo-1,4-dihydro-3-pyridinyl]methyl}carbamate (880 mg, 2.395 mmol) in EtOAc (25 mL) and CH₃Cl (5 mL). The reaction was heated at 40° C. for 4 h, at which time it was diluted with Et₂O (100 mL) and concentrated to provide 3-amino-5-(aminomethyl)-2,6-dimethylpyridin-4(1H)-one (686 mg, 119%) as its bis-hydrochloride salt. ¹H NMR (DMSO-d6) δ 8.17 (br. s., 3H), 3.82-3.92 (m, 2H), 2.52 (s, 3H), 2.44-2.48 (m, 3H), 2.35-2.40 (m, 2H). MS(ES) [M+H]⁺ 168.0.

EXAMPLES

Example 1

N-((2,6-dimethyl-4-oxo-1,4-dihydropyridin-3-yl)methyl)-5-(ethyl(tetrahydro-2H-pyran-4-yl)amino)-4-methylthiophene-3-carboxamide

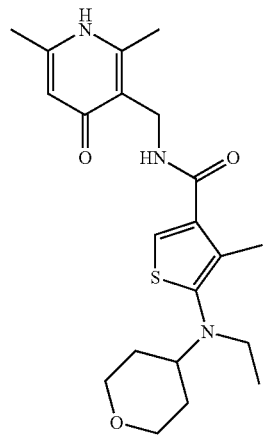

a) Methyl 5-(ethyl(tetrahydro-2H-pyran-4-yl)amino)-4-methylthiophene-3-carboxylate

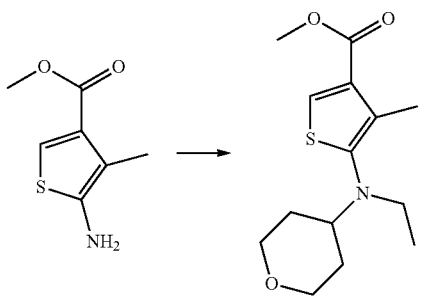

To a solution of commercially available methyl 5-amino-4-methylthiophene-3-carboxylate (500 mg, 2.92 mmol) in DCE (10 mL) were added acetic acid (0.334 mL, 5.84 mmol) and dihydro-2H-pyran-4(3H)-one (322 mg, 3.21 mmol). The reaction was maintained at room temperature for 20 min, at which time NaBH(OAc)$_3$ (2476 mg, 11.68 mmol) was added portion wise. The reaction was stirred for 90 min. LCMS showed the reaction was complete. To the reaction mixture was added acetaldehyde (0.198 mL, 3.50 mmol) and NaBH(OAc)$_3$ (~500 mg). The reaction was stirred for 1 h, at which time it was quenched with sat. NaHCO$_3$, extracted with DCM, and concentrated. The residue was purified by silica gel chromatography (Varian 971IF, 0-50% EtOAc/hexanes, SF25-40 g, 15 minutes) to give methyl 5-(ethyl(tetrahydro-2H-pyran-4-yl)amino)-4-methylthiophene-3-carboxylate (750 mg, 89%) as a tan oil. $^1$H NMR (400 MHz, CDCl3) δ 7.95 (s, 1H) 3.99 (dt, J=10.36, 2.02 Hz, 2H) 3.86 (s, 3H) 3.37 (td, J=11.87, 2.02 Hz, 2H) 2.94-3.04 (m, 3H) 2.35 (s, 3H) 1.75-1.82 (m, 2H) 1.58-1.62 (m, 2H) 0.96 (t, J=7.20 Hz, 3H). MS(ES) [M+H]$^+$ 284.0.

b) N-((2,6-Dimethyl-4-oxo-1,4-dihydropyridin-3-yl)methyl)-5-(ethyl(tetrahydro-2H-pyran-4-yl)amino)-4-methylthiophene-3-carboxamide

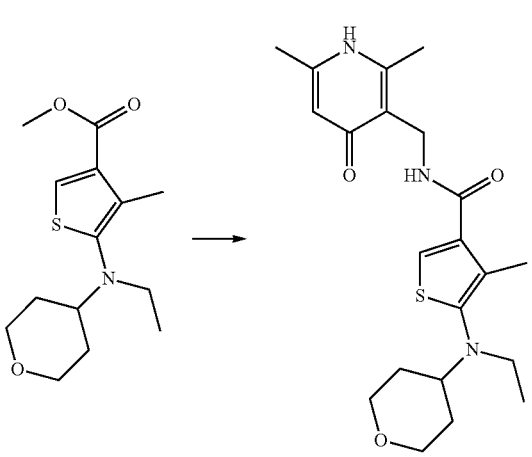

To a solution of methyl 5-(ethyl(tetrahydro-2H-pyran-4-yl)amino)-4-methylthiophene-3-carboxylate (150 mg, 0.529 mmol) in MeOH was added 5 N NaOH (0.529 mL, 2.65 mmol). The reaction was stirred at 40° C. for 2 h. The reaction was allowed to cool to room temperature and was diluted with 6 N HCl (0.441 mL, 2.65 mmol). The mixture was concentrated, diluted with DCM, and concentrated again.

To a solution of the crude residue in DMSO (5 mL) was added NMM (0.291 mL, 2.65 mmol), 3-(aminomethyl)-2,6-dimethylpyridin-4(1H)-one (97 mg, 0.635 mmol), EDC (122 mg, 0.635 mmol), HOBt (97 mg, 0.635 mmol), and more NMM (0.291 mL, 2.65 mmol). The reaction was maintained at room temperature for 75 h, at which time it was purified by reverse phase HPLC (Gilson; 5-60% CH$_3$CN/water+0.1% TFA, YMC ODS-A C18 column 75×30 mm ID S-5 um). The residue was partitioned between EtOAc/MeOH and sat. aqueous NaHCO$_3$. The organic layer was concentrated, diluted with DCM, and concentrated again to provide N-((2,6-dimethyl-4-oxo-1,4-dihydropyridin-3-yl)methyl)-5-(ethyl(tetrahydro-2H-pyran-4-yl)amino)-4-methylthiophene-3-carboxamide (95 mg, 42.3%) as an off-white foam solid. $^1$H NMR (400 MHz, DMSO-d$_6$) δ 11.02 (br. s., 1H) 7.99 (br. s., 1H) 7.64 (s, 1H) 5.88 (br. s., 1H) 4.18 (d, J=5.31 Hz, 2H) 3.83 (d, J=14.15 Hz, 2H) 3.21-3.29 (m, 2H) 2.89-2.95 (m, 3H) 2.32 (s, 3H) 2.14-2.17 (m, 6H) 1.68 (dd, J=12.25, 1.89 Hz, 2H) 1.33-1.44 (m, 2H) 0.85-0.89 (m, 3H). MS(ES) [M+H]$^+$ 404.1.

Example 2

N-((2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide

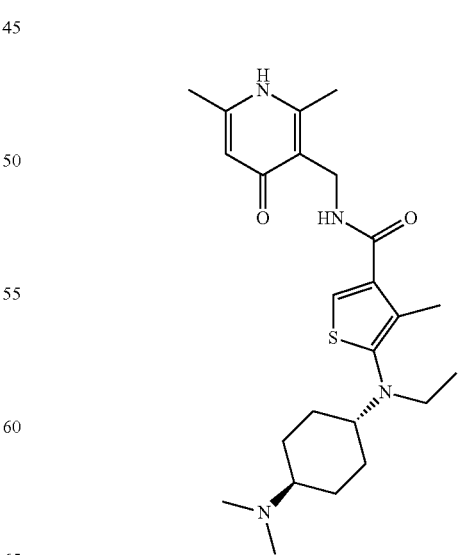

a) Methyl 5-(((cis)-4-(dimethyl amino)cyclohexyl)(ethyl)amino)-4-methylthiophene-3-carboxylate and Methyl 5-(((trans)-4-(dimethyl amino)cyclohexyl)(ethyl)amino)-4-methylthiophene-3-carboxylate

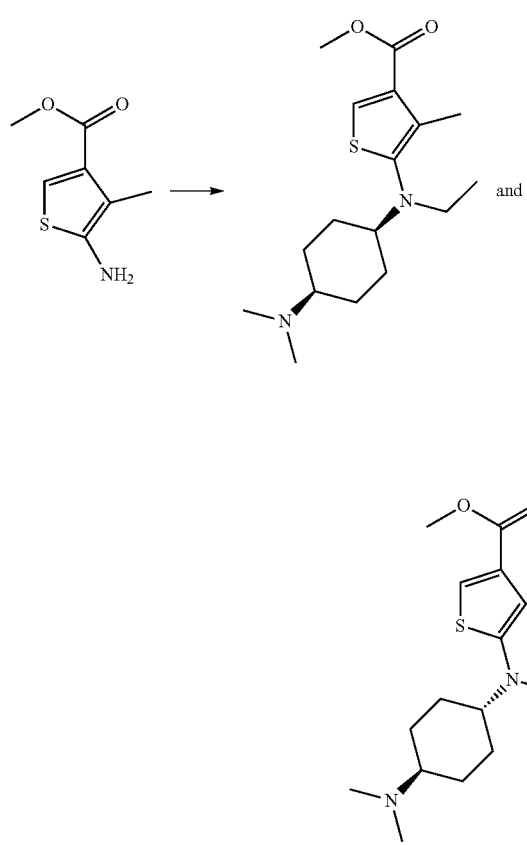

To a solution of methyl 5-amino-4-methylthiophene-3-carboxylate (800 mg, 4.67 mmol) in DCE (25 mL) were added acetic acid (0.535 mL, 9.34 mmol) and 4-(dimethylamino)cyclohexanone (660 mg, 4.67 mmol). The reaction was maintained at room temperature for 40 min, at which time NaBH(OAc)₃ (3961 mg, 18.69 mmol) was added portion-wise. The mixture was stirred at room temperature for 30 min, at which time acetaldehyde (0.317 mL, 5.61 mmol) and more NaBH(OAc)₃ (990 mg, 4.67 mmol) were added. The reaction was stirred for 1 h, at which time it was quenched with NaHCO₃, extracted with DCM, and concentrated. The crude residue was purified by reverse phase Gilson HPLC (10-70% CH₃CN/water+0.1% TFA, YMC ODS-A C18 Column 75×30 mm ID S-5 um, 12 nM Column 6 min). The semi pure residue was partitioned between EtOAc and NaHCO₃ (sat. aq). The organics were concentrated, diluted with DCM and evaporated to provide methyl 5-((4-(dimethylamino)cyclohexyl)(ethyl)amino)-4-methylthiophene-3-carboxylate (mixture of cis and trans isomers) as a brown oil. MS(ES) [M+H]⁺ 325.1.

The cis and trans isomers were separated by chiral HPLC (Gilson; IC 20×250 mm column; 20 mL/min; 5:95 EtOH:Heptane) to give:

Methyl 5-(((cis)-4-(dimethylamino)cyclohexyl)(ethyl)amino)-4-methylthiophene-3-carboxylate (180 mg, 11.87%). ¹H NMR (400 MHz, CDCl₃) δ 7.93 (s, 1H) 3.85 (s, 3H) 2.94-3.00 (m, 3H) 2.37 (s, 3H) 2.28 (s, 6H) 2.16 (br. s., 1H) 1.83-1.91 (m, 2H) 1.71-1.80 (m, 2H) 1.44-1.51 (m, 4H) 0.93 (t, J=7.20 Hz, 3H). MS(ES) [M+H]⁺ 325.2.

Methyl 5-(((trans)-4-(di methylamino)cyclohexyl)(ethyl)amino)-4-methylthiophene-3-carboxylate (387 mg, 25.5%). ¹H NMR (400 MHz, CDCl₃) δ 7.91 (s, 1H) 3.85 (s, 3H) 2.98 (q, J=7.07 Hz, 2H) 2.31 (s, 3H) 2.24-2.28 (m, 6H) 2.10 (m, J=10.89, 7.36, 3.51, 3.51 Hz, 1H) 1.98 (d, J=10.11 Hz, 2H) 1.89-1.93 (m, 2H) 1.20-1.32 (m, 4H) 0.93 (t, J=7.07 Hz, 3H). MS(ES) [M+H]⁺ 325.2.

b) 5-(((trans)-4-(Dimethylamino)cyclohexyl)(ethyl)amino)-4-methylthiophene-3-carboxylic acid

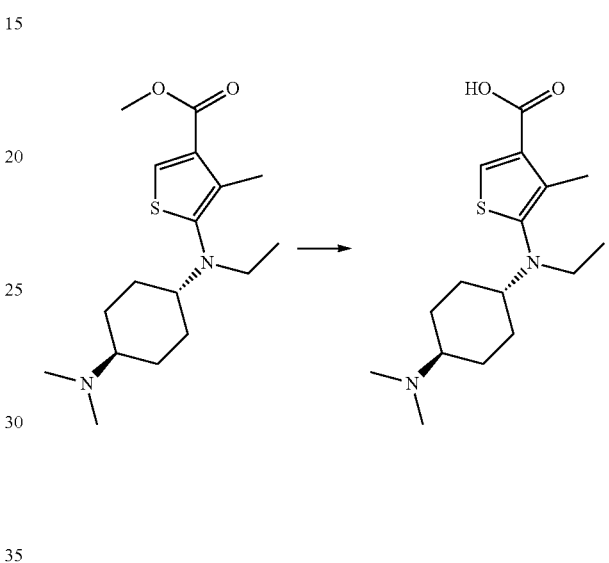

To a solution of methyl 5-(((trans)-4-(dimethylamino)cyclohexyl)(ethyl)amino)-4-methylthiophene-3-carboxylate (380 mg, 1.71 mmol) in MeOH was added 5 N NaOH (1.71 mL, 5.86 mmol). The mixture was stirred overnight at 37° C., at which time 6 N HCl (1.05 mL) was added. The mixture was concentrated to provide 5-(((trans)-4-(dimethylamino)cyclohexyl)(ethyl)amino)-4-methylthiophene-3-carboxylic acid (690 mg, 95%) as a solid. MS(ES) [M+H]⁺ 311.2.

c) N-((2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide

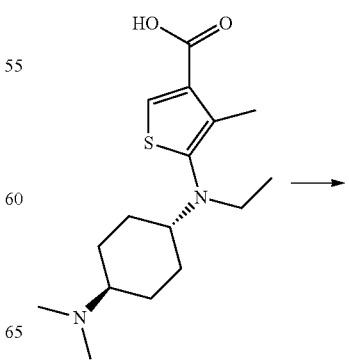

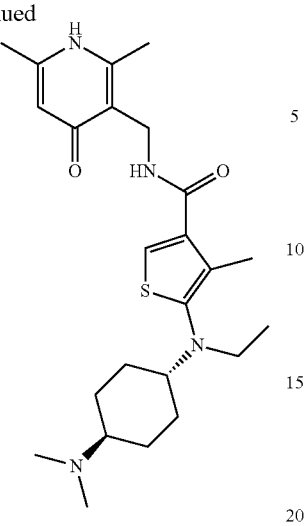

To a solution of 5-(((trans)-4-(dimethylamino)cyclohexyl)(ethyl)amino)-4-methylthiophene-3-carboxylic acid (150 mg, 0.483 mmol) in DMSO (5 mL) were added NMM (0.266 mL, 2.416 mmol) and 3-(aminomethyl)-2,6-dimethylpyridin-4(1H)-one (88 mg, 0.580 mmol), followed by EDC (185 mg, 0.966 mmol), HOBt (148 mg, 0.966 mmol), and more NMM (0.266 mL, 2.416 mmol). The reaction was stirred at room temperature for 12 h. The reaction was purified directly by reverse phase HPLC (Gilson, 5-55% $CH_3CN$/water+0.1% TFA, YMC ODS-A C18 column 75×30 mm ID S-5 um, 12 nM column). The residue was partitioned between EtOAc/MeOH and 0.1N NaOH. The organics were concentrated, diluted with DCM, and concentrated again to provide N-((2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide (80 mg, 35.4%) as an off white foam-solid. $^1$H NMR (600 MHz, DMSO-d6) δ 0.85 (t, J=6.80 Hz, 3H) 1.11-1.24 (m, 4H) 1.77 (d, J=9.82 Hz, 2H) 1.86 (d, J=9.82 Hz, 2H) 2.05 (d, J=8.69 Hz, 1H) 2.12 (br. s., 3H) 2.14 (br. s., 6H) 2.15 (br. s., 3H) 2.31 (s, 3H) 2.66 (br. s., 1H) 2.91 (q, J=6.80 Hz, 2H) 4.17 (d, J=4.15 Hz, 2H) 5.87 (br. s., 1H) 7.59 (s, 1H) 7.94 (br. s., 1H) 11.01 (br. s., 1H). MS(ES) [M+H]$^+$ 445.3. Additional NMR studies (NOE) confirmed the trans geometry.

Example 3

N-((5-amino-2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide

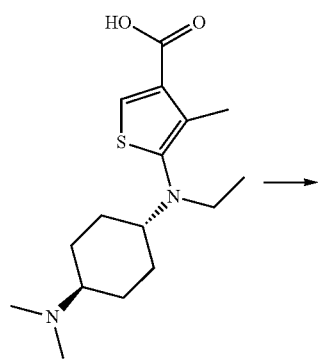

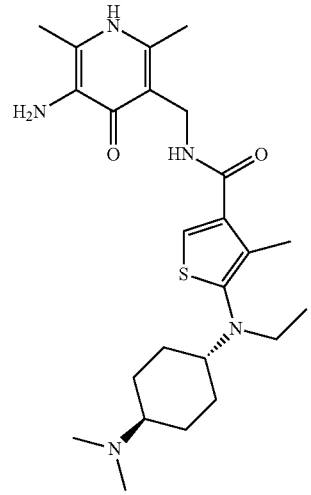

To a solution of 5-(((trans)-4-(dimethylamino)cyclohexyl)(ethyl)amino)-4-methylthiophene-3-carboxylic acid (170 mg, 0.274 mmol) in DMSO (3 mL) were added 3-amino-5-(aminomethyl)-2,6-dimethylpyridin-4(1H)-one bis-hydrochloride (79 mg, 0.324 mmol), HOAt (45 mg, 0.329 mmol), and EDC (63 mg, 0.329 mmol), followed by NMM (2.196 mL, 19.97 mmol). The reaction was stirred at ambient temperature for 2 h, at which time water (2 mL) was added and the reaction was allowed to stand overnight. The reaction was purified directly by prep HPLC (Gilson; Gradient of B: 8-45%, A: water+0.1% TFA, B: $CH_3CN$+0.1% TFA). The resulting residue was dissolved in MeOH/DCM and TEA (0.3 ml), adsorbed onto silica gel, and purified by column chromatography (4 g silica column; Gradient of B: 25-100%, A: DCM, B: 90/10/1 of $CHCl_3$/MeOH/$NH_4OH$). The residue solidified from evaporation with $CH_3CN$, followed by TBME to provide N45-amino-2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide (51 mg, 39%). $^1$H NMR (DMSO-d6) δ 10.82 (s, 1H), 8.01 (t, J=5.1 Hz, 1H), 7.58 (s, 1H), 4.15-4.30 (m, 4H), 2.90 (q, J=6.9 Hz, 2H), 2.65 (d, J=3.3 Hz, 1H), 2.29 (s, 3H), 2.07-2.18 (m, 12H), 2.01 (br. s., 1H), 1.85 (d, J=10.1 Hz, 2H), 1.76 (d, J=9.9 Hz, 2H), 1.12-1.25 (m, 4H), 0.84 (t, J=6.9 Hz, 3H). MS(ES) [M+H]$^+$ 460.3.

Example 4

2-Bromo-N-((2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide

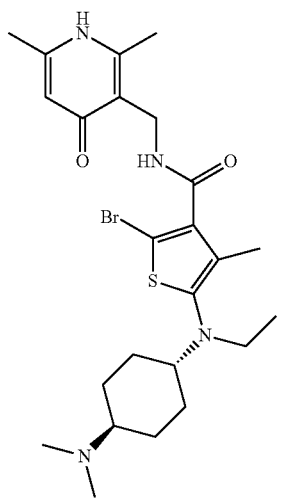 [SMILES: CCN(c1sc(Br)c(C(=O)NCc2c(C)[nH]c(C)cc2=O)c1C)[C@H]1CC[C@H](N(C)C)CC1]

a) Methyl 2-bromo-5-(((trans)-4-(dimethylamino)cyclohexyl)(ethyl)amino)-4-methylthiophene-3-carboxylate

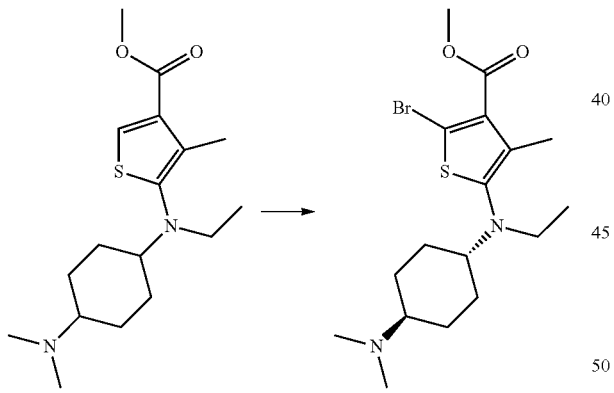

A solution of methyl 5-((4-(dimethylamino)cyclohexyl)(ethyl)amino)-4-methylthiophene-3-carboxylate (5.21 g, 16.06 mmol) in DMF (32 mL) was treated with NBS (4.00 g, 22.48 mmol) and stirred under argon at room temperature for 30 min. The reaction was diluted with water (10 mL) and saturated Na$_2$CO$_3$ solution (pH 9, 1 mL). The resulting suspension was extracted with EtOAc (3×75 mL). The organics were washed with water (50 mL), dried over MgSO$_4$ and concentrated onto silica. The material was purified on an ISCO® Combiflash Rf on 24 g silica using a gradient of CHCl$_3$:MeOH w/1% NH$_4$OH (0-15%). The product fractions were combined and concentrated to afford methyl 2-bromo-5-((4-(dimethylamino)cyclohexyl)(ethyl)amino)-4-methylthiophene-3-carboxylate (3.83 g) as a mixture of cis- and trans-cyclohexyl isomers. The mixture was then separated by HPLC (Chiralpak AD-H, 5 microns, 50 mm×250 mm, 97:3:0.1 CH$_3$CN:isopropylalcohol: isopropylamine, 100 mL/min) to afford methyl 2-bromo-5-(((trans)-4-(dimethylamino)cyclohexyl)(ethyl)amino)-4-methylthiophene-3-carboxylate (2.64 g, 6.41 mmol, 39.9% yield) as an orange tar. $^1$H NMR (400 MHz, CDCl$_3$) δ 3.90 (s, 3H) 2.94 (q, J=7.07 Hz, 2H) 2.64-2.77 (m, 1H) 2.27 (s, 6H) 2.21 (s, 3H) 2.05-2.16 (m, 1H) 1.89-2.00 (m, 4H) 1.16-1.34 (m, 4H) 0.96 (t, J=7.07 Hz, 3H). MS(ES) [M+H]$^+$ 403, 405.

b) 2-Bromo-5-(((trans)-4-(dimethylamino)cyclohexyl)(ethyl)amino)-4-methylthiophene-3-carboxylic acid

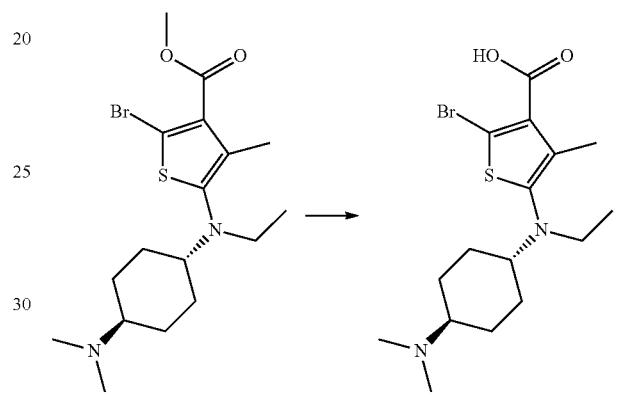

A solution of methyl 2-bromo-5-(((trans)-4-(dimethylamino)cyclohexyl)(ethyl)amino)-4-methylthiophene-3-carboxylate (0.150 g, 0.372 mmol) in MeOH (1.5 mL) and THF (0.300 mL) was treated with 6 M NaOH (0.310 mL, 1.859 mmol). The reaction was heated in a 45° C. oil bath for 18 h. The reaction was neutralized with 5 M HCl (0.372 mL, 1.859 mmol) and concentrated to dryness. MS(ES) [M+H]$^+$ 389.

c) 2-Bromo-N-((2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide

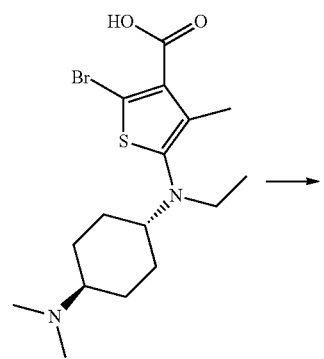

-continued

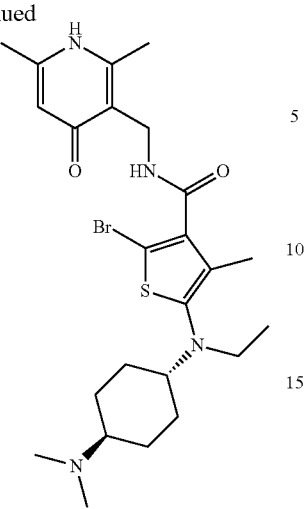

A mixture of 2-bromo-5-(((trans)-4-(dimethylamino)cyclohexyl)(ethyl)amino)-4-methylthiophene-3-carboxylic acid (0.145 g, 0.372 mmol), 3-(aminomethyl)-2,6-dimethylpyridin-4(1H)-one hydrochloride (0.070 g, 0.372 mmol), and DMAP (4.55 mg, 0.037 mmol) in DMSO (2 mL) was added N,N-diisopropylethylamine (0.260 mL, 1.490 mmol), followed by PyBroP® (0.191 g, 0.410 mmol). The reaction was stirred overnight under argon at room temperature. LCMS showed a 2:1 mixture of product to starting material. The reaction was diluted with MeOH (1 mL) and filtered. Purification of the residue by preparative HPLC (Waters Sunfire 30×150 mm column; 10-40% $CH_3CN$/0.1% TFA in water) gave 2-bromo-N-((2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide (54 mg, 26%). $^1$H NMR (400 MHz, DMSO-$d_6$) δ 11.03 (s, 1H) 8.20 (t, J=4.89 Hz, 1H) 5.87 (s, 1H) 4.20 (d, J=4.77 Hz, 2H) 2.88 (q, J=6.86 Hz, 2H) 2.62-2.71 (m, 1H) 2.31 (s, 3H) 2.16 (s, 3H) 2.12 (s, 6H) 1.98-2.07 (m, 1H) 1.92 (s, 3H) 1.85 (d, J=10.04 Hz, 2H) 1.77 (d, J=11.04 Hz, 2H) 1.07-1.26 (m, 4H) 0.89 (t, J=7.03 Hz, 3H). MS(ES) [M+H]$^+$ 523.2.

Assay Protocol 1

Compounds contained herein were evaluated for their ability to inhibit the methyltransferase activity of EZH2 within the PRC2 complex. Human PRC2 complex was prepared by co-expressing each of the 5 member proteins (FLAG-EZH2, EED, SUZ12, RbAp48, AEBP2) in Sf9 cells followed by co-purification. Enzyme activity was measured in a scintillation proximity assay (SPA) where a tritiated methyl group is transferred from 3H-SAM to a lysine residue on Histone H3 of a mononucleosome, purified from HeLa cells. Mononucleosomes were captured on SPA beads and the resulting signal is read on a ViewLux plate reader.

Part A. Compound Preparation
1. Prepare 10 mM stock of compounds from solid in 100% DMSO.
2. Set up an 11-point serial dilution (1:3 dilution, top concentration 10 mM) in 100% DMSO for each test compound in a 384 well plate leaving columns 6 and 18 for DMSO controls.
3. Dispense 100 nL of compound from the dilution plate into reaction plates (Grenier Bio-One, 384-well, Cat#784075).

Part B. Reagent Preparation
Prepare the following solutions:
1. 50 mM Tris-HCl, pH 8: Per 1 L of base buffer, combine 1 M Tris-HCl, pH 8 (50 mL) and distilled water (950 mL).
2. 1× Assay Buffer: Per 10 mL of 1× Assay Buffer, combine 50 mM Tris-HCl, pH 8 (9958 uL), 1 M $MgCl_2$ (20 uL), 2 M DTT (20 uL), and 10% Tween-20 (2 uL) to provide a final concentration of 50 mM Tris-HCl, pH 8, 2 mM $MgCl_2$, 4 mM DTT, 0.002% Tween-20.
3. 2× Enzyme Solution: Per 10 mL of 2× Enzyme Solution, combine 1× Assay Buffer and PRC2 complex to provide a final enzyme concentration of 10 nM.
4. SPA Bead Suspension: Per 1 mL of SPA Bead Suspension, combine PS-PEI coated LEADSeeker beads (40 mg) and $H_2O$ (1 mL) to provide a final concentration of 40 mg/mL.
5. 2× Substrate Solution: Per 10 mL of 2× Substrate Solution, combine 1× Assay Buffer (9728.55 uL), 800 ug/mL mononucleosomes (125 uL), 1 mM cold SAM (4 uL), and 7.02 uM 3H-SAM (142.45 uL; 0.55 mCi/mL) to provide a final concentration of 5 ug/mL nucleosomes, 0.2 uM cold SAM, and 0.05 uM 3H-SAM.
6. 2.67× Quench/Bead Mixture: Per 10 mL of 2.67× Quench/Bead Mixture, combine dd$H_2O$ (9358 uL), 10 mM cold SAM (267 uL), 40 mg/mL Bead Suspension (375 uL) to provide a final concentration of 100 uM cold SAM and 0.5 mg/mL SPA beads.

Part C. Assay Reaction in 384-well Grenier Bio-One Plates
Compound Addition
1. Dispense 100 nL/well of 100× Compound to test wells (as noted above).
2. Dispense 100 nL/well of 100% DMSO to columns 6 & 18 for high and low controls, respectively.

Assay
1. Dispense 5 uL/well of 1× Assay Buffer to column 18 (low control reactions).
2. Dispense 5 uL/well of 2× Enzyme Solution to columns 1-17, 19-24.
3. Spin assay plates for 1 min at 500 rpm.
4. Stack the assay plates, covering the top plate.
5. Incubate the compound/DMSO with the enzyme for 30 min at room temperature.
6. Dispense 5 uL/well of 2× Substrate Solution to columns 1-24.
7. Spin assay plates for ~1 min at 500 rpm.
8. Stack the assay plates, covering the top plate.
9. Incubate the assay plates at room temperature for 1 hour.

Quench/Bead Addition
1. Dispense 5 uL/well of the 3× Quench/Bead Mixture to columns 1-24.
2. Seal the top of each assay plate with adhesive TopSeal.
3. Spin assay plates for ~1 min at 500 rpm.
4. Equilibrate the plates for >20 min.

Read plates
1. Read the assay plates on the Viewlux Plate Reader utilizing the 613 nm emission filter with a 300 s read time.

Reagent addition can be done manually or with automated liquid handler.
*The final DMSO concentration in this assay is 1%.
*The positive control is in column 6; negative control is in column 18.
*Final starting concentration of compounds is 100 μM.

Results

Percent inhibition was calculated relative to the DMSO control for each compound concentration and the resulting values were fit using standard $IC_{50}$ fitting parameters within the ABASE data fitting software package.

The compounds of Examples 1-3 were generally tested according to the above or an analogous assay and were found to be inhibitors of EZH2. Specific biological activities tested according to such assays are listed in the following table. Repeating the assay run(s) may result in somewhat different $IC_{50}$ values.

| Example | EZH2 $IC_{50}$ (nM) |
| --- | --- |
| 1 | 316 |
| 2 | 32 |
| 3 | 32 |

Assay Protocol 2

Compounds contained herein were evaluated for their ability to inhibit the methyltransferase activity of EZH2 within the PRC2 complex. Human PRC2 complex was prepared by co-expressing each of the 5 member proteins (FLAG-EZH2, EED, SUZ12, RbAp48, AEBP2) in Sf9 cells followed by co-purification. Enzyme activity was measured in a scintillation proximity assay (SPA) where a tritiated methyl group is transferred from 3H-SAM to a lysine residue on a biotinylated, unmethylated peptide substrate derived from histone H3. The peptides were captured on streptavidin-coated SPA beads and the resulting signal was read on a ViewLux plate reader.

Part A. Compound Preparation
  4. Prepare 10 mM stock of compounds from solid in 100% DMSO.
  5. Set up an 11-point serial dilution (1:4 dilution, top concentration 10 mM) in 100% DMSO for each test compound in a 384 well plate leaving columns 6 and 18 for DMSO controls.
  6. Dispense 10 nL of compound from the dilution plate into reaction plates (Corning, 384-well polystyrene NBS, Cat#3673).

Part B. Reagent Preparation
Prepare the following solutions:
  7. 1× Base Buffer, 50 mM Tris-HCl, pH 8, 2 mM $MgCl_2$: Per 1 L of base buffer, combine 1 M Tris-HCl, pH 8 (50 mL), 1 M $MgCl_2$ (2 mL), and distilled water (948 mL).
  8. 1× Assay Buffer: Per 10 mL of 1× Assay Buffer, combine 1× Base Buffer (9.96 mL), 1 M DTT (40 uL), and 10% Tween-20 (1 uL) to provide a final concentration of 50 mM Tris-HCl, pH 8, 2 mM $MgCl_2$, 4 mM DTT, 0.001% Tween-20.
  9. 2× Enzyme Solution: Per 10 mL of 2× Enzyme Solution, combine 1× Assay Buffer (9.99 mL) and 3.24 uM EZH2 5 member complex (6.17 uL) to provide a final enzyme concentration of 1 nM.
  10. SPA Bead Solution: Per 1 mL of SPA Bead Solution, combine Streptavidin coated SPA beads (PerkinElmer, Cat# RPNQ0261, 40 mg) and 1× Assay Buffer (1 mL) to provide a working concentration of 40 mg/mL.
  11. 2× Substrate Solution: Per 10 mL of 2× Substrate Solution, combine 40 mg/mL SPA Bead Solution (375 uL), 1 mM biotinylated histone H3K27 peptide (200 uL), 12.5 uM 3H-SAM (240 uL; 1 mCi/mL), 1 mM cold SAM (57 uL), and 1× Assay Buffer (9.13 mL) to provide a final concentration of 0.75 mg/mL SPA Bead Solution, 10 uM biotinylated histone H3K27 peptide, 0.15 uM 3H-SAM (~12 uCi/mL 3H-SAM), and 2.85 uM cold SAM.
  12. 2.67× Quench Solution: Per 10 mL of 2.67× Quench Solution, combine 1× Assay Buffer (9.73 mL) and 10 mM cold SAM (267 uL) to provide a final concentration of 100 uM cold SAM.

Part C. Assay Reaction in 384-well Grenier Bio-One Plates
Compound Addition
  3. Stamp 10 nL/well of 1000× Compound to test wells (as noted above).
  4. Stamp 10 nL/well of 100% DMSO to columns 6 & 18 (high and low controls, respectively).

Assay
  10. Dispense 5 uL/well of 1× Assay Buffer to column 18 (low control reactions).
  11. Dispense 5 uL/well of 2× Substrate Solution to columns 1-24 (note: substrate solution should be mixed to ensure homogeneous bead suspension before dispensing into matrix reservoir).
  12. Dispense 5 uL/well of 2× Enzyme Solution to columns 1-17, 19 24.
  13. Incubate the reaction for 60 min at room temperature.

Quench
  5. Dispense 6 uL/well of the 2.67× Quench Solution to columns 1-24.
  6. Seal assay plates and spin for ~1 min at 500 rpm.
  7. Dark adapt plates in the ViewLux instrument for 15-60 min.

Read plates
  2. Read the assay plates on the Viewlux Plate Reader utilizing the 613 nm emission filter or clear filter (300 s exposure).

Reagent addition can be done manually or with automated liquid handler.

Results

Percent inhibition was calculated relative to the DMSO control for each compound concentration and the resulting values were fit using standard $IC_{50}$ fitting parameters within the ABASE data fitting software package.

The compounds of Examples 2-4 were generally tested according to the above or an analogous assay and were found to be inhibitors of EZH2. Specific biological activities tested according to such assays are listed in the following table. Repeating the assay run(s) may result in somewhat different $IC_{50}$ values.

| Example | EZH2 $IC_{50}$ (nM) |
| --- | --- |
| 2 | 100 |
| 3 | 16 |
| 4 | 160 |

The invention claimed is:
1. A compound according to Formula (I):

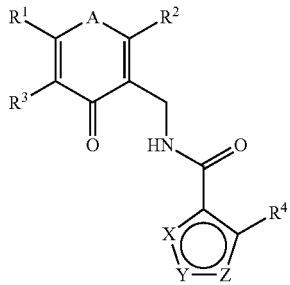

wherein:
A is NH;
X is O, N, S, CR$^6$, or NR$^7$;
Y is O, N, S, CR$^6$, or NR$^7$;
Z is CR$^5$ or NR$^8$; wherein when X is O, S, or NR$^7$, Y is N or CR$^6$ and Z is CR$^5$; when Y is O, S, or NR$^7$, X is N or CR$^6$ and Z is CR$^5$; and when Z is NR$^8$, Y is N or CR$^6$ and X is N or CR$^6$;
R$^1$, R$^2$, and R$^3$ are each independently selected from the group consisting of hydrogen, (C$_1$-C$_4$)alkoxy, (C$_1$-C$_8$)alkyl, (C$_1$-C$_4$)alkoxy(C$_1$-C$_4$)alkyl-, halo(C$_1$-C$_4$)alkyl, (C$_3$-C$_8$)cycloalkyl, hydroxy(C$_1$-C$_4$)alkyl, (C$_3$-C$_8$)cycloalkyl(C$_1$-C$_4$)alkyl-, R$^a$O(O)CNH(C$_1$-C$_4$)alkyl-, (C$_6$-C$_{10}$)bicycloalkyl, heterocycloalkyl, heterocycloalkyl(C$_1$-C$_4$)alkyl-, aryl, aryl(C$_1$-C$_4$)alkyl, heteroaryl, heteroaryl(C$_1$-C$_4$)alkyl, halogen, cyano, —C(O)R$^a$, —CO$_2$R$^a$, —C(O)NR$^a$R$^b$, —C(O)NR$^a$NR$^a$R$^b$, —SR$^a$, —S(O)R$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —NR$^a$NR$^a$C(O)OR$^a$, —OR$^a$, —OC(O)R$^a$, and —OC(O)NR$^a$R$^b$, wherein each (C$_3$-C$_8$)cycloalkyl, (C$_6$-C$_{10}$)bicycloalkyl, heterocycloalkyl, aryl, or heteroaryl is optionally substituted 1, 2, or 3 times, independently, by hydroxyl, halogen, nitro, (C$_1$-C$_4$)alkyl, cyano, (C$_1$-C$_4$)alkoxy, —NR$^a$R$^b$ or —CO$_2$R$^a$;
R$^4$ is selected from the group consisting of hydrogen, (C$_1$-C$_3$)alkoxy, (C$_1$-C$_3$)alkyl, hydroxyl, halogen, cyano, (C$_3$-C$_6$)cycloalkyl, heterocycloalkyl, —NR$^a$R$^b$, halo(C$_1$-C$_3$)alkyl, and hydroxy(C$_1$-C$_3$)alkyl;
R$^5$ is selected from the group consisting of (C$_4$-C$_8$)alkyl, (C$_2$-C$_8$)alkenyl, (C$_3$-C$_8$)alkoxy, (C$_4$-C$_8$)cycloalkyl, (C$_3$-C$_8$)cycloalkyl(C$_1$-C$_2$)alkyl-, (C$_3$-C$_8$)cycloalkyloxy-, heterocycloalkyl, heterocycloalkyl(C$_1$-C$_2$)alkyl-, heterocycloalkyloxy-, aryl, heteroaryl, and —NR$^a$R$^b$, wherein said (C$_4$-C$_8$)alkyl, (C$_2$-C$_8$)alkenyl, (C$_3$-C$_8$)alkoxy, (C$_4$-C$_8$)cycloalkyl, (C$_3$-C$_8$)cycloalkyl(C$_1$-C$_2$)alkyl-, (C$_3$-C$_8$)cycloalkyloxy-, heterocycloalkyl, heterocycloalkyl(C$_1$-C$_2$)alkyl-, heterocycloalkyloxy-, aryl, or heteroaryl is optionally substituted 1, 2, or 3 times, independently, by halogen, —OR$^a$, —NR$^a$R$^b$, —NHCO$_2$R$^a$, nitro, (C$_1$-C$_3$)alkyl, R$^a$R$^b$N(C$_1$-C$_3$)alkyl-, R$^a$O(C$_1$-C$_3$)alkyl-, (C$_3$-C$_8$)cycloalkyl, cyano, —CO$_2$R$^a$, —C(O)NR$^a$R$^b$, —SO$_2$NR$^a$R$^b$, heterocycloalkyl, aryl, or heteroaryl, wherein said (C$_3$-C$_8$)cycloalkyl, heterocycloalkyl, aryl, or heteroaryl is optionally substituted 1 or 2 times, independently, by halogen, (C$_1$-C$_4$)alkyl, halo(C$_1$-C$_4$)alkyl, —CO(C$_1$-C$_4$)alkyl, —CO$_2$(C$_1$-C$_4$)alkyl, —NR$^a$R$^b$, —NHCO$_2$R$^a$, hydroxyl, oxo, (C$_1$-C$_4$)alkoxy, or (C$_1$-C$_4$)alkoxy(C$_1$-C$_4$)alkyl-; or any 2 optional substituents on said (C$_2$-C$_8$)alkenyl taken together with the carbon atom(s) to which they are attached represent a 5-8 membered ring, optionally containing a heteroatom selected from oxygen, nitrogen, and sulfur, wherein said ring is optionally substituted 1 or 2 times, independently, by (C$_1$-C$_4$)alkyl, halo(C$_1$-C$_4$)alkyl, —CO(C$_1$-C$_4$)alkyl, —CO$_2$(C$_1$-C$_4$)alkyl, —NR$^a$R$^b$, —NHCO$_2$R$^a$, hydroxyl, oxo, (C$_1$-C$_4$)alkoxy, or (C$_1$-C$_4$)alkoxy(C$_1$-C$_4$)alkyl-;
R$^6$ is selected from the group consisting of hydrogen, halogen, (C$_1$-C$_8$)alkyl, (C$_1$-C$_4$)alkoxy, —B(OH)$_2$, (C$_3$-C$_8$)cycloalkyl, (C$_3$-C$_8$)cycloalkyl(C$_1$-C$_4$)alkyl-, (C$_6$-C$_{10}$)bicycloalkyl, heterocycloalkyl, heterocycloalkyl(C$_1$-C$_4$)alkyl-, aryl, aryl(C$_1$-C$_4$)alkyl, heteroaryl, heteroaryl(C$_1$-C$_4$)alkyl, cyano, —C(O)R$^a$, —CO$_2$R$^a$, —C(O)NR$^a$R$^b$, —C(O)NR$^a$NR$^a$R$^b$, —SR$^a$, —S(O)R$^a$, —SO$_2$R$^a$, —SO$_2$NR$^a$R$^b$, nitro, —NR$^a$R$^b$, R$^a$R$^b$N(C$_1$-C$_4$)alkyl-, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —NR$^a$NR$^a$C(O)OR$^a$, —OR$^a$, —OC(O)R$^a$, and —OC(O)NR$^a$R$^b$, wherein each cycloalkyl, bicycloalkyl, heterocycloalkyl, aryl, or heteroaryl group is optionally substituted 1, 2, or 3 times, independently, by R$^c$—(C$_1$-C$_6$)alkyl-O—, R$^c$—(C$_1$-C$_6$)alkyl-S—, R$^c$—(C$_1$-C$_6$)alkyl-, (C$_1$-C$_4$)alkyl-heterocycloalkyl-, halogen, (C$_1$-C$_6$)alkyl, (C$_3$-C$_8$)cycloalkyl, halo(C$_1$-C$_6$)alkyl, cyano, —C(O)R$^a$, —CO$_2$R$^a$, —C(O)NR$^a$R$^b$, —SR$^a$, —S(O)R$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, heterocycloalkyl, aryl, heteroaryl, aryl(C$_1$-C$_4$)alkyl, or heteroaryl(C$_1$-C$_4$)alkyl;
R$^7$ is selected from the group consisting of hydrogen, (C$_1$-C$_8$)alkyl, (C$_3$-C$_8$)cycloalkyl, (C$_3$-C$_8$)cycloalkyl(C$_1$-C$_4$)alkyl-, (C$_6$-C$_{10}$)bicycloalkyl, heterocycloalkyl, heterocycloalkyl(C$_1$-C$_4$)alkyl-, aryl, aryl(C$_1$-C$_4$)alkyl, heteroaryl, heteroaryl(C$_1$-C$_4$)alkyl, —C(O)R$^a$, —CO$_2$R$^a$, —C(O)NR$^a$R$^b$, —C(O)NR$^a$NR$^a$R$^b$, —SO$_2$R$^a$, —SO$_2$NR$^a$R$^b$, and R$^a$R$^b$N(C$_1$-C$_4$)alkyl-, wherein each cycloalkyl, bicycloalkyl, heterocycloalkyl, aryl, or heteroaryl group is optionally substituted 1, 2, or 3 times, independently, by R$^c$—(C$_1$-C$_6$)alkyl-O—, R$^c$—(C$_1$-C$_6$)alkyl-, (C$_1$-C$_4$)alkyl-heterocycloalkyl-, halogen, (C$_1$-C$_6$)alkyl, (C$_3$-C$_8$)cycloalkyl, halo(C$_1$-C$_6$)alkyl, cyano, —C(O)R$^a$, —CO$_2$R$^a$, —C(O)NR$^a$R$^b$, —SR$^a$, —S(O)R$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, heterocycloalkyl, aryl, heteroaryl, aryl(C$_1$-C$_4$)alkyl, or heteroaryl(C$_1$-C$_4$)alkyl;
R$^8$ is selected from the group consisting of (C$_4$-C$_8$)alkyl, (C$_4$-C$_8$)cycloalkyl, heterocycloalkyl, heterocycloalkyl(C$_1$-C$_2$)alkyl-, aryl, and heteroaryl, wherein said (C$_4$-C$_8$)alkyl, (C$_4$-C$_8$)cycloalkyl, heterocycloalkyl, heterocycloalkyl(C$_1$-C$_2$)alkyl-, aryl, or heteroaryl is optionally substituted 1, 2, or 3 times, independently, by halogen, —OR$^a$, —NR$^a$R$^b$, —NHCO$_2$R$^a$, nitro, (C$_1$-C$_3$)alkyl, R$^a$R$^b$N(C$_1$-C$_3$)alkyl-, R$^a$O(C$_1$-C$_3$)alkyl-, (C$_3$-C$_8$)cycloalkyl, cyano, —CO$_2$R$^a$, —C(O)NR$^a$R$^b$, —SO$_2$NR$^a$R$^b$, aryl, or heteroaryl;
each R$^c$ is independently —S(O)R$^a$, —SO$_2$R$^a$, —NR$^a$R$^b$, —NR$^a$C(O)OR$^a$, —NR$^a$SO$_2$R$^b$, or —CO$_2$R$^a$; and $R^a$ and $R^b$ are each independently hydrogen, $(C_1-C_4)$alkyl, $(C_1-C_4)$alkoxy$(C_1-C_4)$alkyl-, $(C_3-C_{10})$cycloalkyl, heterocycloalkyl, aryl, aryl$(C_1-C_4)$alkyl-, heteroaryl$(C_1-C_4)$alkyl-, or heteroaryl, wherein any said cycloalkyl, heterocycloalkyl, aryl, or heteroaryl group is optionally substituted 1, 2, or 3 times, independently, by halogen, hydroxyl, $(C_1-C_4)$alkoxy, amino, —NH$(C_1-C_4)$alkyl, —N$((C_1-C_4)$alkyl$)_2$, $(C_1-C_4)$alkyl, halo$(C_1-C_4)$alkyl, —CO$_2$H, —CO$_2(C_1-C_4)$alkyl, —CONH$_2$, —CONH$(C_1-C_4)$alkyl, —CON$((C_1-C_4)$alkyl$)_2$, —SO$_2(C_1-C_4)$alkyl, —SO$_2$NH$_2$, —SO$_2$NH$(C_1-C_4)$alkyl, or —SO$_2$N$((C_1-C_4)$alkyl$)_2$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted 1, 2, or 3 times, independently, by $(C_1-C_4)$alkyl, halo$(C_1-C_4)$alkyl, amino, —NH$(C_1-C_4)$alkyl, —N$((C_1-C_4)$alkyl$)_2$, hydroxyl, oxo, $(C_1-C_4)$alkoxy, or $(C_1-C_4)$alkoxy$(C_1-C_4)$alkyl-, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

or a pharmaceutically acceptable salt thereof.

2. The compound according to claim 1 represented by Formula (III)(a):

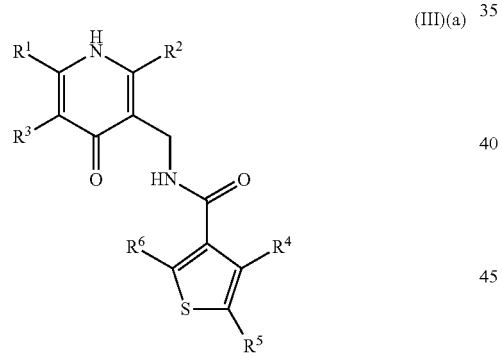

(III)(a)

wherein:

$R^1$, $R^2$, and $R^3$ are each independently selected from the group consisting of hydrogen, $(C_1-C_4)$alkoxy, $(C_1-C_8)$alkyl, $(C_1-C_4)$alkoxy$(C_1-C_4)$alkyl-, halo$(C_1-C_4)$alkyl, $(C_3-C_8)$cycloalkyl, hydroxy$(C_1-C_4)$alkyl, $(C_3-C_8)$cycloalkyl$(C_1-C_4)$alkyl-, $R^aO(O)CNH(C_1-C_4)$alkyl-, $(C_6-C_{10})$bicycloalkyl, heterocycloalkyl, heterocycloalkyl$(C_1-C_4)$alkyl-, aryl, aryl$(C_1-C_4)$alkyl, heteroaryl, heteroaryl$(C_1-C_4)$alkyl, halogen, cyano, —C(O)$R^a$, —CO$_2R^a$, —C(O)NR$^aR^b$, —C(O)NR$^a$NR$^aR^b$, —SR$^a$, —S(O)R$^a$, —SO$_2R^a$, —SO$_2$NR$^aR^b$, nitro, —NR$^aR^b$, —NR$^a$C(O)R$^b$, —NR$^a$C(O)NR$^aR^b$, —NR$^a$C(O)OR$^a$, —NR$^a$SO$_2R^b$, —NR$^a$SO$_2$NR$^aR^b$, —NR$^a$NR$^aR^b$, —NR$^a$NR$^a$C(O)R$^b$, —NR$^a$NR$^a$C(O)NR$^aR^b$, —NR$^a$NR$^a$C(O)OR$^a$, —OR$^a$, —OC(O)R$^a$, and —OC(O)NR$^aR^b$, wherein each $(C_3-C_8)$cycloalkyl, $(C_6-C_{10})$bicycloalkyl, heterocycloalkyl, aryl, or heteroaryl is optionally substituted 1, 2, or 3 times, independently, by hydroxyl, halogen, nitro, $(C_1-C_4)$alkyl, cyano, $(C_1-C_4)$alkoxy, —NR$^aR^b$ or —CO$_2R^a$;

$R^4$ is selected from the group consisting of hydrogen, $(C_1-C_3)$alkoxy, $(C_1-C_3)$alkyl, hydroxyl, halogen, cyano, $(C_3-C_6)$cycloalkyl, heterocycloalkyl, —NR$^aR^b$, halo$(C_1-C_3)$alkyl, and hydroxy$(C_1-C_3)$alkyl;

$R^5$ is selected from the group consisting of $(C_4-C_8)$alkyl, $(C_3-C_8)$alkoxy, $(C_4-C_8)$cycloalkyl, $(C_3-C_8)$cycloalkyloxy-, heterocycloalkyl, heterocycloalkyloxy-, aryl, heteroaryl, and —NR$^aR^b$, wherein said $(C_4-C_8)$alkyl, $(C_3-C_8)$alkoxy, $(C_4-C_8)$cycloalkyl, $(C_3-C_8)$cycloalkyloxy-, heterocycloalkyl, heterocycloalkyloxy-, aryl, or heteroaryl is optionally substituted 1, 2, or 3 times, independently, by halogen, —OR$^a$, —NR$^aR^b$, —NHCO$_2R^a$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —CO$_2R^a$, —C(O)NR$^aR^b$, —SO$_2$NR$^aR^b$, aryl, or heteroaryl;

$R^6$ is selected from the group consisting of hydrogen, halogen, $(C_1-C_8)$alkyl, $(C_1-C_4)$alkoxy, —B(OH)$_2$, $(C_3-C_8)$cycloalkyl, $(C_3-C_8)$cycloalkyl$(C_1-C_4)$alkyl-, $(C_6-C_{10})$bicycloalkyl, heterocycloalkyl, heterocycloalkyl$(C_1-C_4)$alkyl-, aryl, aryl$(C_1-C_4)$alkyl, heteroaryl, heteroaryl$(C_1-C_4)$alkyl, cyano, —C(O)R$^a$, —CO$_2R^a$, —C(O)NR$^aR^b$, —C(O)NR$^a$NR$^aR^b$, —SR$^a$, —S(O)R$^a$, —SO$_2R^a$, —SO$_2$NR$^aR^b$, nitro, —NR$^aR^b$, $R^aR^bN(C_1-C_4)$alkyl-, —NR$^a$C(O)R$^b$, —NR$^a$C(O)NR$^aR^b$, —NR$^a$C(O)OR$^a$, —NR$^a$SO$_2R^b$, —NR$^a$SO$_2$NR$^aR^b$, —NR$^a$NR$^aR^b$, —NR$^a$NR$^a$C(O)R$^b$, —NR$^a$NR$^a$C(O)NR$^aR^b$, —NR$^a$NR$^a$C(O)OR$^a$, —OR$^a$, —OC(O)R$^a$, and —OC(O)NR$^aR^b$, wherein each cycloalkyl, bicycloalkyl, heterocycloalkyl, aryl, or heteroaryl group is optionally substituted 1, 2, or 3 times, independently, by $R^c$—$(C_1-C_6)$alkyl-O—, $(C_1-C_4)$alkyl-heterocycloalkyl-, halogen, $(C_1-C_6)$alkyl, $(C_3-C_8)$cycloalkyl, halo$(C_1-C_6)$alkyl, cyano, —C(O)R$^a$, —CO$_2R^a$, —C(O)NR$^aR^b$, —SR$^a$, —S(O)R$^a$, —SO$_2R^a$, —SO$_2$NR$^aR^b$, nitro, —NR$^aR^b$, —NR$^a$C(O)R$^b$, —NR$^a$C(O)NR$^aR^b$, —NR$^a$C(O)OR$^a$, —NR$^a$SO$_2R^b$, —NR$^a$SO$_2$NR$^aR^b$, —OR$^a$, —OC(O)R$^a$, —OC(O)NR$^aR^b$, heterocycloalkyl, aryl, heteroaryl, aryl$(C_1-C_4)$alkyl, or heteroaryl$(C_1-C_4)$alkyl;

each $R^c$ is independently —S(O)R$^a$, —SO$_2R^a$, —NR$^aR^b$, —NR$^a$C(O)OR$^a$, —NR$^a$SO$_2R^b$, or —CO$_2R^a$; and $R^a$ and $R^b$ are each independently hydrogen, $(C_1-C_4)$alkyl, $(C_1-C_4)$alkoxy$(C_1-C_4)$alkyl-, $(C_3-C_{10})$cycloalkyl, heterocycloalkyl, aryl, aryl$(C_1-C_4)$alkyl-, heteroaryl$(C_1-C_4)$alkyl-, or heteroaryl, wherein any said cycloalkyl, heterocycloalkyl, aryl, or heteroaryl group is optionally substituted 1, 2, or 3 times, independently, by halogen, hydroxyl, $(C_1-C_4)$alkoxy, amino, —NH$(C_1-C_4)$alkyl, —N$((C_1-C_4)$alkyl$)_2$, $(C_1-C_4)$alkyl, halo$(C_1-C_4)$alkyl, —CO$_2$H, —CO$_2(C_1-C_4)$alkyl, —CONH$_2$, —CONH$(C_1-C_4)$alkyl, —CON$((C_1-C_4)$alkyl$)_2$, —SO$_2(C_1-C_4)$alkyl, —SO$_2$NH$_2$, —SO$_2$NH$(C_1-C_4)$alkyl, or —SO$_2$N$((C_1-C_4)$alkyl$)_2$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted 1, 2, or 3 times, independently, by $(C_1-C_4)$alkyl, halo$(C_1-C_4)$alkyl, amino, —NH$(C_1-C_4)$alkyl, —N$((C_1-C_4)$alkyl$)_2$, hydroxyl, oxo, $(C_1-C_4)$alkoxy, or $(C_1-C_4)$alkoxy$(C_1-C_4)$alkyl-, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a ($C_3$-$C_8$)cycloalkyl, heterocycloalkyl, aryl, or heteroaryl ring;

or a pharmaceutically acceptable salt thereof.

3. The compound according to claim 1, wherein $R^1$ and $R^2$ are each independently ($C_1$-$C_4$)alkyl, or a pharmaceutically acceptable salt thereof.

4. The compound according to claim 2, wherein:
$R^1$ and $R^2$ are each independently ($C_1$-$C_4$)alkyl;
$R^3$ is hydrogen;
$R^4$ is selected from the group consisting of ($C_1$-$C_3$)alkyl and halogen;
$R^5$ is —$NR^aR^b$;
$R^6$ is hydrogen, halogen, ($C_1$-$C_4$)alkyl, or ($C_1$-$C_4$)alkoxy;
$R^a$ is azetidinyl, oxetanyl, pyrrolidinyl, piperidinyl, piperazinyl, morpholinyl, thiomorpholinyl, or tetrahydropyranyl, each of which is optionally substituted 1 or 2 times, independently, by ($C_1$-$C_4$)alkyl; or
$R^a$ is cyclopentyl or cyclohexyl, each of which is optionally substituted by amino, —NH($C_1$-$C_4$)alkyl, or —N(($C_1$-$C_4$)alkyl)$_2$; and
$R^b$ is hydrogen or ($C_1$-$C_4$)alkyl;
or a pharmaceutically acceptable salt thereof.

5. The compound according to claim 1, wherein $R^3$ is hydrogen, or a pharmaceutically acceptable salt thereof.

6. The compound according to claim 1, wherein $R^4$ is selected from the group consisting of ($C_1$-$C_3$)alkyl and halogen, or a pharmaceutically acceptable salt thereof.

7. The compound according to claim 1, wherein $R^5$ is selected from the group consisting of ($C_3$-$C_6$)alkoxy, ($C_3$-$C_6$)cycloalkyloxy-, heterocycloalkyloxy-, heterocycloalkyl, —NH(($C_3$-$C_6$)cycloalkyl), —N(($C_1$-$C_3$)alkyl)(($C_3$-$C_6$)cycloalkyl), —NH(heterocycloalkyl), and —N(($C_1$-$C_3$)alkyl)(heterocycloalkyl), wherein any said ($C_3$-$C_6$)alkoxy, ($C_3$-$C_6$)cycloalkyloxy-, heterocycloalkyloxy-, heterocycloalkyl, or ($C_3$-$C_6$)cycloalkyl is optionally substituted 1 or 2 times, independently, by halogen, hydroxyl, ($C_1$-$C_3$)alkoxy, amino, —NH($C_1$-$C_3$)alkyl, —N(($C_1$-$C_3$)alkyl)$_2$, ($C_1$-$C_3$)alkyl, ($C_1$-$C_3$)alkoxy($C_1$-$C_3$)alkyl-, amino($C_1$-$C_3$)alkyl-, (($C_1$-$C_3$)alkyl)NH($C_1$-$C_3$)alkyl-, (($C_1$-$C_3$)alkyl)$_2$N($C_1$-$C_3$)alkyl-, ($C_3$-$C_8$)cycloalkyl, cyano, —$CO_2R^a$, —$C(O)NR^aR^b$, —$SO_2NR^aR^b$, phenyl, or heteroaryl, or a pharmaceutically acceptable salt thereof.

8. The compound according to claim 7, wherein $R^5$ is selected from the group consisting of ($C_3$-$C_6$)alkoxy, ($C_3$-$C_8$)cycloalkyloxy-, and heterocycloalkyloxy-, each of which is optionally substituted by hydroxyl, ($C_1$-$C_3$)alkoxy, amino, —NH($C_1$-$C_3$)alkyl, —N(($C_1$-$C_3$)alkyl)$_2$, ($C_1$-$C_3$)alkyl, —$CO_2R^a$, —$C(O)NR^aR^b$, —$SO_2NR^aR^b$, phenyl, or heteroaryl, or a pharmaceutically acceptable salt thereof.

9. The compound according to claim 7, wherein $R^5$ is selected from the group consisting of cyclopentyloxy, cyclohexyloxy, pyrrolidinyloxy, piperidinyloxy, and tetrahydropyranyloxy, each of which is optionally substituted by hydroxyl, ($C_1$-$C_3$)alkoxy, amino, —NH($C_1$-$C_3$)alkyl, —N(($C_1$-$C_3$)alkyl)$_2$, ($C_1$-$C_3$)alkyl, —$CO_2R^a$, —$C(O)NR^aR^b$, —$SO_2NR^aR^b$, phenyl, furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, or pyrimidinyl, wherein $R^a$ is ($C_1$-$C_4$)alkyl or phenyl($C_1$-$C_2$)alkyl and $R^b$ is hydrogen or ($C_1$-$C_4$)alkyl, or a pharmaceutically acceptable salt thereof.

10. The compound according to claim 1, wherein $R^5$ is —$NR^aR^b$, or a pharmaceutically acceptable salt thereof.

11. The compound according to claim 10, wherein $R^a$ is azetidinyl, oxetanyl, pyrrolidinyl, piperidinyl, piperazinyl, morpholinyl, thiomorpholinyl, or tetrahydropyranyl, each of which is optionally substituted 1 or 2 times, independently, by ($C_1$-$C_4$)alkyl, and $R^b$ is hydrogen or ($C_1$-$C_4$)alkyl, or a pharmaceutically acceptable salt thereof.

12. The compound according to claim 10, wherein $R^a$ is cyclopentyl or cyclohexyl, each of which is optionally substituted by amino, —NH($C_1$-$C_4$)alkyl, or —N(($C_1$-$C_4$)alkyl)$_2$, and $R^b$ is hydrogen or ($C_1$-$C_4$)alkyl, or a pharmaceutically acceptable salt thereof.

13. The compound according to claim 1, wherein $R^6$ is selected from the group consisting of hydrogen, —$SO_2$($C_1$-$C_4$)alkyl, halogen, ($C_1$-$C_6$)alkyl, ($C_1$-$C_4$)alkoxy, phenyl, heteroaryl, and cyano, wherein said phenyl or heteroaryl group is optionally substituted 1 or 2 times, independently, by ($C_1$-$C_4$)alkoxy, —$NR^aR^b$, $R^aR^bN$($C_1$-$C_4$)alkyl-, ($C_1$-$C_4$)alkylheterocycloalkyl-, halogen, ($C_1$-$C_4$)alkyl, ($C_3$-$C_8$)cycloalkyl, or heterocycloalkyl, or a pharmaceutically acceptable salt thereof.

14. The compound according to claim 13, wherein $R^6$ is hydrogen, halogen, ($C_1$-$C_4$)alkyl, or ($C_1$-$C_4$)alkoxy, or a pharmaceutically acceptable salt thereof.

15. The compound according to claim 13, wherein $R^6$ is hydrogen, fluorine, chlorine, or bromine, or a pharmaceutically acceptable salt thereof.

16. The compound according to claim 1, wherein $R^7$ is selected from the group consisting of hydrogen, ($C_1$-$C_6$)alkyl, ($C_3$-$C_6$)cycloalkyl, phenyl, and heteroaryl, wherein said phenyl or heteroaryl group is optionally substituted 1 or 2 times, independently, by ($C_1$-$C_4$)alkoxy, —$NR^aR^b$, $R^aR^bN$($C_1$-$C_4$)alkyl-, ($C_1$-$C_4$)alkylheterocycloalkyl-, halogen, ($C_1$-$C_4$)alkyl, ($C_3$-$C_8$)cycloalkyl, or heterocycloalkyl, or a pharmaceutically acceptable salt thereof.

17. The compound according to claim 16, wherein $R^7$ is hydrogen or ($C_1$-$C_4$)alkyl, or a pharmaceutically acceptable salt thereof.

18. The compound according to claim 1, wherein $R^8$ is selected from the group consisting of ($C_4$-$C_6$)alkyl, ($C_4$-$C_6$)cycloalkyl, heterocycloalkyl, and phenyl, wherein said ($C_4$-$C_6$)alkyl, ($C_4$-$C_6$)cycloalkyl, heterocycloalkyl, or phenyl is optionally substituted 1 or 2 times, independently, by —$OR^a$, —$NR^aR^b$, —$NHCO_2R^a$, ($C_1$-$C_3$)alkyl, $R^aR^bN$($C_1$-$C_3$)alkyl-, $R^aO$($C_1$-$C_3$)alkyl-, —$CO_2R^a$, —$C(O)NR^aR^b$, or —$SO_2NR^aR^b$, or a pharmaceutically acceptable salt thereof.

19. The compound according to claim 1 which is:
N-((2,6-dimethyl-4-oxo-1,4-dihydropyridin-3-yl)methyl)-5-(ethyl(tetrahydro-2H-pyran-4-yl)amino)-4-methylthiophene-3-carboxamide;
N-((2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide;
N-((5-amino-2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide; or
2-bromo-N-((2,6-dimethyl-4-oxo-1,4-dihydropyridin-3-yl)methyl)-5-(((trans)-4-(dimethylamino)cyclohexyl)(ethyl)amino)-4-methylthiophene-3-carboxamide;
or a pharmaceutically acceptable salt thereof.

20. A pharmaceutical composition comprising the compound or pharmaceutically acceptable salt thereof according to claim 1 and a pharmaceutically acceptable excipient.

* * * * *